United States Patent
Claremon et al.

(10) Patent No.: US 8,598,160 B2
(45) Date of Patent: Dec. 3, 2013

(54) CYCLOALKYL LACTAME DERIVATIVES AS INHIBITORS OF 11-BETA-HYDROXYSTEROID DEHYDROGENASE 1

(75) Inventors: David A. Claremon, Maple Glen, PA (US); Linghang Zhuang, Chalfont, PA (US); Yuanjie Ye, Ambler, PA (US); Suresh B. Singh, Kendall Park, NJ (US); Colin M. Tice, Ambler, PA (US); Robert D. Simpson, Wilmington, DE (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 111 days.

(21) Appl. No.: 12/867,374

(22) PCT Filed: Feb. 13, 2009

(86) PCT No.: PCT/US2009/000908
§ 371 (c)(1),
(2), (4) Date: Nov. 2, 2010

(87) PCT Pub. No.: WO2009/102460
PCT Pub. Date: Aug. 20, 2009

(65) Prior Publication Data
US 2011/0071139 A1 Mar. 24, 2011

Related U.S. Application Data

(60) Provisional application No. 61/065,890, filed on Feb. 15, 2008.

(51) Int. Cl.
| | |
|---|---|
| C07D 211/16 | (2006.01) |
| C07D 243/04 | (2006.01) |
| C07D 265/10 | (2006.01) |
| A61K 31/4402 | (2006.01) |
| A61P 3/04 | (2006.01) |

(52) U.S. Cl.
USPC .......................................... 514/218; 540/492

(58) Field of Classification Search
USPC .......................................... 540/492; 514/218
See application file for complete search history.

(56) References Cited

U.S. PATENT DOCUMENTS

| | | | |
|---|---|---|---|
| 3,341,538 A | 9/1967 | Block et al. | |
| 3,378,587 A | 4/1968 | Reinhardt | |
| 3,681,349 A | 8/1972 | Schwan et al. | |
| 3,703,529 A | 11/1972 | Frederick et al. | |
| 3,919,047 A | 11/1975 | Vidic et al. | |
| 4,009,171 A | 2/1977 | Albertson | |
| 4,043,927 A | 8/1977 | Duling et al. | |
| 4,108,857 A | 8/1978 | Albertson | |
| 4,136,145 A | 1/1979 | Fuchs et al. | |
| 4,136,162 A | 1/1979 | Fuchs et al. | |
| 5,089,506 A | 2/1992 | Gray et al. | |
| 5,098,916 A | 3/1992 | Gray et al. | |
| 5,215,992 A | 6/1993 | Gray et al. | |
| 5,393,735 A | 2/1995 | Lange et al. | |
| 5,410,081 A | 4/1995 | Kunde et al. | |
| 5,432,175 A | 7/1995 | Piwinski et al. | |
| 5,480,899 A | 1/1996 | Yano et al. | |
| 5,502,027 A | 3/1996 | Lange et al. | |
| 5,631,209 A | 5/1997 | Lange et al. | |
| 5,776,959 A | 7/1998 | Covey et al. | |
| 5,780,466 A | 7/1998 | Emonds-Alt et al. | |
| 5,811,422 A | 9/1998 | Lam et al. | |
| 5,856,273 A | 1/1999 | Kay et al. | |
| 5,866,702 A | 2/1999 | Mackman et al. | |
| 5,936,124 A | 8/1999 | Hilborn et al. | |
| 5,981,436 A | 11/1999 | Drewes et al. | |
| 6,066,666 A | 5/2000 | Covey et al. | |
| 6,159,990 A | 12/2000 | Lagu et al. | |
| 6,242,637 B1 | 6/2001 | Emonds-Alt et al. | |

(Continued)

FOREIGN PATENT DOCUMENTS

| | | |
|---|---|---|
| DE | 1801556 A1 | 5/1970 |
| DE | 2 105 743 A1 | 8/1972 |

(Continued)

OTHER PUBLICATIONS

International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.

(Continued)

*Primary Examiner* — Bruck Kifle
(74) *Attorney, Agent, or Firm* — McCarter & English LLP; Steven G. Davis; Michael J. DeGrazia

(57) ABSTRACT

This invention relates to novel compounds of the Formula (I), any of the formulas $I_1$-$I_{26}$ $1a_{1-3}$-$1j_{1-3}$ or pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to cortisol in a cell.

(I)

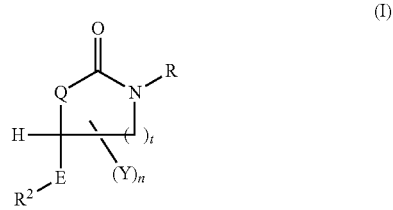

15 Claims, No Drawings

(56) References Cited

U.S. PATENT DOCUMENTS

| | | |
|---|---|---|
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 2 108 954 A1 | 9/1972 |
| DE | 2 229 695 A1 | 1/1974 |
| DE | 23 38 369 A1 | 2/1975 |
| DE | 23 54 002 A1 | 5/1975 |
| DE | 2 411 382 A1 | 9/1975 |
| DE | 2 437 610 A1 | 2/1976 |
| DE | 2 828 039 A1 | 1/1980 |
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0 847 275 A1 | 6/1998 |
| EP | 0928789 A1 | 7/1999 |
| EP | 1156049 A | 11/2001 |
| EP | 1270724 A2 | 1/2003 |
| EP | 1801098 A1 | 6/2007 |
| EP | 1852425 A | 11/2007 |
| EP | 1 864 971 A1 | 12/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |

(56) References Cited

FOREIGN PATENT DOCUMENTS

| | | |
|---|---|---|
| JP | 2007 254409 | 10/2007 |
| JP | 2011519374 A | 7/2011 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | 96/37494 A1 | 11/1996 |
| WO | 97/07789 A1 | 3/1997 |
| WO | WO 97/36605 | 10/1997 |
| WO | 98/22462 A1 | 5/1998 |
| WO | WO 98/57940 | 12/1998 |
| WO | WO 99/05125 | 2/1999 |
| WO | WO 99/06395 | 2/1999 |
| WO | 0009107 A2 | 2/2000 |
| WO | WO 01/00595 A1 | 1/2001 |
| WO | 0113917 A1 | 3/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | 03/097608 A2 | 11/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | 2004/046137 A1 | 6/2004 |
| WO | 2004056745 A2 | 7/2004 |
| WO | 2004/089896 A1 | 10/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | 2005116002 A2 | 12/2005 |
| WO | WO 2005/113525 A1 | 12/2005 |
| WO | 2006002349 A1 | 1/2006 |
| WO | WO 2006/003494 A2 | 1/2006 |
| WO | 2006017443 | 2/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | 2006/109056 A1 | 10/2006 |
| WO | WO 2006/104280 A | 10/2006 |
| WO | WO 2007/008529 A2 | 1/2007 |
| WO | 2007/022371 A2 | 2/2007 |
| WO | 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | 2007/076055 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | 2007101270 A1 | 9/2007 |
| WO | 2007103719 A2 | 9/2007 |
| WO | WO 2007/109456 A2 | 9/2007 |
| WO | WO 2007/118185 A2 | 10/2007 |
| WO | 2007/123853 A2 | 11/2007 |
| WO | 2007/127763 A2 | 11/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | 2008024497 A2 | 2/2008 |
| WO | WO 2008/031227 A1 | 3/2008 |
| WO | WO 2008/036715 A1 | 3/2008 |
| WO | 2008/046578 A2 | 4/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | 2009020140 A1 | 2/2009 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | 2009/107664 A1 | 9/2009 |
| WO | 2009108332 A1 | 9/2009 |
| WO | WO 2009/117109 | 9/2009 |
| WO | 2009131669 A2 | 10/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | 2010/010150 A1 | 1/2010 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | 2010089303 A1 | 8/2010 |
| WO | WO 2010/091067 | 8/2010 |
| WO | 2010104830 A1 | 9/2010 |
| WO | WO 2010/127237 | 11/2010 |
| WO | 2010/139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011/057054 A1 | 5/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

Vippagunta, et al., "Crystalline Solids", Advanced Drug Deliver Reviews, 2001, vol. 48, pp. 3-26.
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/933,027 filed Mar. 18, 2009, Vitae Pharmaceuticals, Inc.

(56) References Cited

OTHER PUBLICATIONS

U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract, (1969).
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract, (1978).
Zhurnal Organicheskoi Khimii, 1978, vol. 14(5), pp. 1092-1094.
Database CA [Online], Chemical Abstracts Service, Fukushima et al., "Preparation of Imidazolidinone Derivatives as 11.beta.-HSD1 Inhibitors", XP 002531878, (1983).
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4- pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
International Search Report—(PCT/US2010/023021) Date of Mailing Aug. 5, 2010.
Anderson, (Chem and Biol 10:787-797, 2003).
Bosch et al.: Heterocycles 1980, 14, p. 1983-1988.
CA 1267843-31-1, (Aug. 10, 2009).
CA 154:284276, (Mar . 17, 2011).

(56) References Cited

OTHER PUBLICATIONS

Caplus-133:4656—Anantanarayan, A. el. al., "Preparation of heteroarylpyrazoles as P38 kinase inhibitors". 2000.
Caplus-147:134403, Hembrough, TA, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
Chalmers (TIPS vol. 17, pp. 166-172 Apr. 1996).
Chemical Abstracts, Registry No. 351443-37-3 (Available on Aug. 15, 2001.).
Claremon et al. CAS: 150:214405, 2009.
DeMarinis R.M. et.al. Journal of Medicinal Chemistry 1981, vol. 24, No. 12, pp. 1432-1437.
Examiner Interview Summary dated May 2, 2011, in U.S. Appl. No. 12/741,522 (U.S. Patent No. 8,138,178).
Gutkowska et al.: Acta Polonaie Pharmaceutica 1987, 39, p. 411-414.
Gutkowska et al.: Acta Poloniae Pharmaceutica 1986, 43, p. 403-405.
Gutkowska et al.: Acta Poloniae Pharmaceutica, 1982, vol. 39, p. 61-64.
Harno et.al. Trends in Endocrinology and Metabolism, Elsevier Science Publishing, New York 2010, vol. 21, No. 10, pp. 619-627.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report and Written Opinion for PCT/EP2009/059509, mailed Feb. 9, 2009.
International Search Report and Written Opinion for PCT/US2012/050679 mailed Oct. 31, 2012.
International Search Report for PCT/EP2009/063913 mailed May 6, 2010.
Ma et al.: Synthesis 2007, p. 161-163.
Ma et al.: Tetrahedron 2007, 63, p. 7523-7531.
Morissette et al. Advanced Drug Deliery Reviews 2004, 56, 275-300.
Office Action dated Apr. 3, 2012 for corresponding U.S. Appl. No. 13/318,271.
Office Action dated Jun. 14, 2012 for corresponding U.S. Appl. No. 13/347,784.
Office Action dated May 3, 2012 for corresponding U.S. Appl. No. 13/347,799.
Office Action for U.S. Appl. No. 12/741,522 (U.S. Patent No. 8,138,178), date of mailing Dec. 15, 2010.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Olesen et al.: Current Opin Drug Dis Dev, 2001, vol. 4, No. 4, p. 471-478.
Rosenstock et.al. Diabetes Care Jul. 2010, LNKDPUBMED: 20413513, vol. 33, No. 7, pp. 1516-1522.
Souillac et al., Characterization of Delivery Systems, Differential Scanning Calorimetry, pp. 217-218 (in Encyclopedia of Controlled Drug Delivery, 1999, John Wiley & Sons, pp. 212-227).
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968).

Taddayon et.al. Expert opinion on Investigational Drugs, Ashley Publication Ltd. 2003, vol. 12, No. 3, pp. 307-324.
Thiel (Nature Biotechnol 2:513-519, 2004).
Thornber et al.: Chem Soc Rev, 1979, vol. 8, p. 563-580.
Vidic et al.: Chem. Ber. 1976, 109, p. 2657-2669.
Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
Yokoyama et al.: J. Med. Chem. 1979, 22, p. 537-553.
Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.
Evans, B.E. et al., "Orally active, nonpeptide osytocin antagonists". Journal of Medicinal Chemistry, American Chem. Soc., Vo. 35, No. 21, Oct. 15, 1992, p. 3919-3927.
Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.
Aluri. B.R. et al., "Bulky n-Substituted 1,3-Benzazaphospholes: Access via Pd-Catalyzed C—N and C—P Cross Coupling, Lithiation, and Conversion to Novel P=C PtBu2 Hybrid Ligands". Inorganic Chemistry, 2008, 47, p. 6900-6912.
Aluri, B.R. et al., "Sterically and Polarity-Controlled Reactions of tBuLi with P=CH—NR Heterocycles: Novel Heterocyclic P-and P,O-Ligands and Preliminary Tests in Transition-Metal Catalysis", Chem. Eur. Journal, vol. 14, 2008, p. 4328-4335.
Fandrick, Dr. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.
International Search Report and Written Opinion for PCT/EP12009/059496 mailed Nov. 17, 2009.
International Search Report and Written Opinion for PCT/EP2010/051262 mailed May 3, 2010.
International Search Report and Written Opinion for PCT/EP2011/060386 mailed Sep. 16, 2011.
International Search Report and Written Opinion for PCT/US2010/054912 mailed Mar. 16, 2011.
International Search Report for PCT/EP2011/068938 mailed Mar. 27, 2012.
Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.
Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.
Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.
Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.
Worthy, Ad. et al., "Regioselective Hydroformylation of Sulfonamides using a Scaffolding Ligand". Organic Letters, 2009, vol. 11, No. 13—p. 2764-2767.

CYCLOALKYL LACTAME DERIVATIVES AS INHIBITORS OF 11-BETA-HYDROXYSTEROID DEHYDROGENASE 1

RELATED APPLICATIONS

This application is the U.S. National Stage of PCT International Application Number PCT/US2009/000908, filed Feb. 13, 2009, which claims the benefit of U.S. Provisional Application No. 61/065,890, filed on Feb. 15, 2008, the entire teachings of which are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell, Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), $4^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts thereof, are effective inhibitors of 11β-HSD1. Formula I and its constituent members are defined herein as follows:

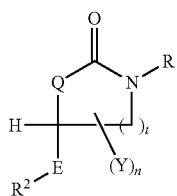

R is

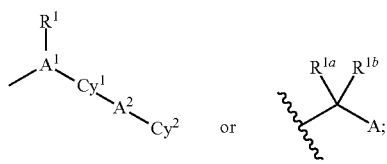

R¹ is (a) absent or (b) is selected from $(C_1-C_6)$alkyl, $(C_2-C_6)$alkenyl, $(C_2-C_6)$alkynyl or $(C_1-C_3)$alkoxy$(C_1-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl; $(C_1-C_6)$alkylcarbonyl; $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl; provided that if (a) t is 2 and Q is O or $CH_2$ or t is 1 and Q is 0, (b) $A^1$ is $CH_2$ optionally substituted with $R_1$ and (c) $A^2$ is a bond, then $Cy^2$ is meta or para to the ring atom of $Cy^1$ that is bonded to $A^1$ and the aryl, heteroaryl, monocyclic cycloalkyl or heterocyclyl, represented by $Cy^1$ is not substituted with bromine, iodine, amino, halo$(C_1-C_6)$alkyl at a ring atom ortho to the carbon atom bounded to $A^1$;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkyl-alkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocycisulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino ($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl; ($C_1$-$C_6$)alkylcarbonyl; ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

provided that if (a) t is 1; (b) Q is 0, (c) $A^1$ is $CH_2$ optionally substituted with $R^1$ and (d) $Cy^1$ is phenyl then $A^2Cy^2$ is not $NHR^4$ or optionally substituted heterocyclyl;

provided that if (a) $A^1$ is $CH_2CH_2O$; (b) $Cy^1$ is phenyl and (c) $A^2$ is $CH_2$ then $Cy^2$ is not heterocyclyl substituted with oxo;

$R^{1a}$ and $R^{1b}$ are each independently selected from (a) hydrogen or (b) ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl which are optionally substituted with up to three groups independently selected from fluorine, hydroxy, ($C_1$-$C_3$)alkoxy and $H_2NC(=O)$;

A is straight or branched ($C_1$-$C_6$)alkyl, ($C_2$-$C_8$)alkenyl or ($C_2$-$C_8$)alkynyl, optionally substituted with up to 4 groups independently selected from fluorine, cyano, oxo, $R^4$, —OH $R^{40}$—, $(R^4)_2N$—, $R^4O_2C$—, $R^4S$—, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4SO_2NR^4$—, $R^4S(=O)_2NHC(=O)$—, $R^4S(=O)_2NHC(=O)O$—, $R^4S(=O)_2NHC(=O)NR^4$—, $R^{40}S(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo);

t is 1, 2 or 3;

Y is ($C_1$-$C_6$)alkyl or halo($C_1$-$C_6$)alkyl;

n is 0, 1 or 2;

E is (a) a bond or (b) ($C_1$-$C_3$)alkylene or ($C_1$-$C_2$)alkylenyloxy, wherein the 0 is attached to $R^2$, each of which is optionally substituted with 1 to 4 groups independently selected from methyl, ethyl, trifluoromethyl or oxo; provided that if Q is NH, then $ER^2$ is not ($C_1$-$C_6$)alkyl or benzyl;

$R^2$ is ($C_1$-$C_6$)alkyl, aryl, heteroaryl, cycloalkyl or heterocyclyl, wherein each is optionally substituted with up to 4 groups independently selected from fluorine, chlorine, bromine, iodine, nitro, hydroxy, ($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl ($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl; ($C_1$-$C_6$)alkylcarbonyl; ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_r$, $C_6$)alkyl}aminocarbonyl($C_1$-$C_6$)alkyl and di($C_3$-$C_6$)cycloalkylaminocarbonyl($C_1$-$C_6$)alkyl;

wherein the 1 to 4 substituents for the group represented by $R^2$ are additionally selected from: amino, cyano, carboxy, ($C_1$-$C_6$)alkoxycarbonyl and hydroxy($C_1$-$C_6$)alkyl, when E is bond or ($C_1$-$C_3$)alkylene, t is 1 and Q is O or $CH_2$, provided that $ER^2$ is not $CH_2Cl$, $CH_2OH$, CHO or $CH_2O$ phenyl;

provided that when (a) t is 2; (b) E is bond and (c) $R^2$ is phenyl, then $R^2$ is not substituted with ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy;

provided that when (a) $A^1$ is bond; (b) $R^1$ is absent; (c) $Cy^1$ is phenyl; (d) $A^2$ is bond (e) $Cy^2$ is H and (f) E is bond, then $R^2$ is not unsubstituted phenyl;

provided that when (a) t is 1; (b) Q is $NR^5$; (c) $A^1$ is bond; (d) $R^1$ is absent; (e) $Cy^1$ is optionally substituted phenyl; (f) $A^2$ is bond; (g) $Cy^2$ is H then $ER^2$ is not unsubstituted (C1-C6) alkyl;

Q is O, $NR^5$ or $CH_2$;

each $R^4$ is independently selected from H, ($C_1$-$C_6$)alkyl, halo($C_1$-$C_6$)alkyl, amino($C_1$-$C_6$)alkyl, ($C_1$-$C_6$)alkylamino ($C_1$-$C_6$)alkyl, di($C_1$-$C_6$)alkylamino($C_1$-$C_6$)alkyl, hydroxy ($C_1$-$C_6$)alkyl and ($C_1$-$C_6$)alkoxy($C_1$-$C_6$)alkyl; and each $R^5$ is independently H, ($C_1$-$C_6$)alkyl, halo($C_1$-$C_6$)alkyl, or hydroxy($C_1$-$C_6$)alkyl;

or a pharmaceutically acceptable salt, enantiomer or diastereomer thereof.

Another embodiment is a pharmaceutical composition comprising: i) a pharmaceutically acceptable carrier or diluent; and ii) compound of Formulas I, $I_1$-$I_{26}$, $Ia_{1-3}$, $Ib_{1-3}$, $Ic_{1-3}$, $Id_{1-3}$, $Ie_{1-3}$, $Ig_{1-3}$, $Ih_{1-3}$, $Ii_{1-3}$ or $Ij_{1-3}$ or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas I, $I_1$-$I_{26}$, $Ia_{1-3}$, $Ic_{1-3}$, $Ic_{1-3}$, $Ie_{1-3}$, $If_{1-3}$, $Ig_{1-3}$, $Ih_{1-3}$, $Ii_{1-3}$ or $Ij_{1-3}$ or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, $I_1$-$I_{26}$, $Ia_{1-3}$, $Ib_{1-3}$, $Ic_{1-3}$, $Id_{1-3}$, $Ie_{1-3}$, $If_{1-3}$, $Ig_{1-3}$, $Ih_{1-3}$, $Ii_{1-3}$ or $Ij_{1-3}$ or a pharmaceutically acceptable salt, enantiomer or diastereomer thereof.

Another embodiment of the invention is the use of a compound of Formulas I, $I_1$-$I_{26}$, $Ia_{1-3}$, $Ib_{1-3}$, $Ic_{1-3}$, $Id_{1-3}$, $Ie_{1-3}$, $If_{1-3}$, $Ig_{1-3}$, $Ih_{1-3}$, $Ii_{1-3}$ or $Ij_{1-3}$ or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of I $I_1$-$I_{26}$ $Ia_{1-3}$, $Ib_{1-3}$, $Ic_{1-3}$, $Id_{1-3}$, $Ie_{1-3}$, $Id_{1-3}$, $Ig_{1-3}$, $Ih_{1-3}$, $Ii_{1-3}$ or $Ij_{1-3}$ or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, $I_1$-$I_{26}$ $Ia_{1-3}$, $Ib_{1-3}$, $Ic_{1-3}$, $Id_{1-3}$, $Ie_{1-3}$, $Id_{1-3}$, $Ig_{1-3}$, $Ih_{1-3}$, $Ii_{1-3}$ or $Ij_{1-3}$ or a pharmaceutically acceptable salt, enantiomer or diastereomer thereof for use in inhibiting 11β-HSD1 activity in a mammal in need of such treatment.

Another embodiment of the invention is a compound of Formulas I, $I_1$-$I_{26}$ $Ia_{1-3}$, $Ib_{1-3}$, $Ic_{1-3}$, $Id_{1-3}$, $Ie_{1-3}$, $Id_{1-3}$, $Ig_{1-3}$, $Ih_{1-3}$, $Ii_{1-3}$ or $Ij_{1-3}$ or a pharmaceutically acceptable salt, enantiomer or diastereomer thereof for use in for treating a subject with a disease associated with the activity or expression of 11β-HSD1.

The present invention further provides methods of inhibiting 11β-HSD1 by contacting 11β-HSD1 with a compound of Formula I, $I_1$-$I_{26}$ $Ia_{1-3}$, $Ib_{1-3}$, $Ic_{1-3}$, $Id_{1-3}$, $Ie_{1-3}$, $If_{1-3}$, $Ig_{1-3}$, $Ih_{1-3}$, $Ii_{1-3}$ or $Ij_{1-3}$ of the invention.

The present invention further provides methods of inhibiting or reducing the conversion of cortisone to cortisol in a cell using a compound of Formula I, $I_1$-$I_{26}$ $Ia_{1-3}$, $Ib_{1-3}$, $Ic_{1-3}$, $Id_{1-3}$, $Ie_{1-3}$, $If_{1-3}$, $Ig_{1-3}$, $Ih_{1-3}$ or $Ij_{1-3}$ of the invention.

The present invention further provides methods of inhibiting or reducing production of cortisol in a cell using a compound of Formula I, $I_1$-$I_{26}$ $Ia_{1-3}$, $Ib_{1-3}$, $Ic_{1-3}$, $Id_{1-3}$, $Ie_{1-3}$, $If_{1-3}$, $Ig_{1-3}$, $Ih_{1-3}$, $Ii_{1-3}$ or $Ij_{1-3}$ of the invention.

The present invention further provides methods of increasing insulin sensitivity in a subject in need thereof using a compound of Formula I, $I_1$-$I_{26}$ $Ia_{1-3}$, $Ib_{1-3}$, $Ic_{1-3}$, $Id_{1-3}$, $Ie_{1-3}$, $If_{1-3}$, $Ig_{1-3}$, $Ih_{1-3}$, $Ii_{1-3}$ or $Ij_{1-3}$ of the invention.

DETAILED DESCRIPTION OF THE INVENTION

The present invention proivds novel compounds that are effective inhibitors of 11β-hydroxysteroid dehydrogenase type 1 (11β-HSD1).

Values and alternative values for the variables in the above-described Structural Formula I are provided herein:

$R^1$ is (a) absent or (b) is selected from ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl, wherein each is optionally substituted with up to four groups independently selected from fluorine, cyano, oxo, $R^4$, $R^{40}$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^{40}S(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino. In another embodiment, $R^1$ is ($C_1$-$C_6$)alkyl. In another embodiment, $R^1$ is absent or is optionally substituted methyl or ethyl. Alternatively, $R^1$ is an optionally substituted methyl or ethyl. In yet another embodiment $R^1$ is unsubstituted.

$A^1$ is (a) a bond, or (b) ($C_1$-$C_3$)alkylene, $CH_2CH_2O$, wherein the oxygen is attached to $Cy^1$, or $CH_2C(=O)$, wherein the carbonyl carbon is attached to $Cy^1$. In another embodiment, $A^1$ is ($C_1$-$C_3$)alkylene. Alternatively, $A^1$ is ($C_2$-$C_3$)alkylene. In another embodiment, $A^1$ is a bond. In yet another embodiment $A^1$ is methylene. Alternatively, $A^1$ is a bond.

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl; provided that if (a) t is 2 and Q is O or $CH_2$ or t is 1 and Q is 0, (b) $A^1$ is $CH_2$ optionally substituted with $R_1$ and (c) $A_2$ is a bond, then $Cy^2$ is meta or para to the ring atom of $Cy^1$ that is bonded to $A^1$ and the aryl, heteroaryl, monocyclic cycloalkyl or heterocyclyl, represented by $Cy^1$ is not substituted with bromine, iodine, amino, halo($C_1$-$C_6$)alkyl at a ring atom ortho to the carbon atom bounded to $A_1$. In another embodiment, $Cy^1$ is optionally substituted aryl or optionally substituted heteroaryl. In another embodiment, $Cy^1$ is optionally substituted phenyl, cyclohexyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy and 2-hydroxy-2-methylpropoxy. In another embodiment, $Cy^1$ is optionally substituted phenyl or optionally substituted pyridyl. Alternatively, $Cy^1$ is optionally substituted phenyl. In another embodiment, $Cy^1$ is phenyl substituted with fluorine, or bromine.

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo. In another embodiment, $A^2$ is a bond, O or $OCH_2CO$. In another embodiment, $A^2$ is a bond.

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$) alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo ($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo ($C_3$-$C_6$)cycloalkyl, halo($C_4$-$C_7$)cycloalkylalkyl, ($C_1$-$C_6$) alkoxy, ($C_3$-$C_6$)cycloalkoxy, ($C_4$-$C_7$)cycloalkylalkoxy, halo ($C_1$-$C_6$)alkoxy, halo($C_3$-$C_6$)cycloalkoxy, halo($C_4$-$C_7$) cycloalkylalkoxy, ($C_1$-$C_6$)alkylthio, ($C_3$-$C_6$)cycloalkylhio, ($C_4$-$C_7$)cycloalkyl-alkylthio, halo($C_1$-$C_6$)alkylthio, halo($C_3$-$C_6$)cycloalkylhio, halo($C_4$-$C_7$)cycloalkylalkylthio, ($C_1$-$C_6$) alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$) cycloalkylalkanesulfinyl, ($C_1$-$C_6$)alkanesulfonyl, ($C_3$-$C_6$) cycloalkanesulfonyl, ($C_4$-$C_7$)cycloalkylalkanesulfonyl, halo ($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo ($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$) alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$) alkylcarbonylamino, ($C_1$-$C_6$)alkylcarbonylamino($C_1$-$C_6$) alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$) alkyl, hydroxy($C_1$-$C_6$)alkoxy, heteroaryl, oxo, amino($C_1$-$C_6$) alkyl, ($C_1$-$C_6$)alkylamino($C_1$-$C_6$)alkyl, di($C_1$-$C_6$)alkylamino ($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$) alkylcarbonyl; provided that if (a) t is 1; (b) Q is 0, (c) $A^1$ is $CH_2$ optionally substituted with $R_1$ and (d) $Cy^1$ is phenyl then $A_2Cy^2$ is not $NHR^4$ and $Cy^2$ is not optionally substituted heterocyclyl. In another embodiment, $Cy^2$ is optionally substituted aryl or optionally substituted heteroaryl. In another embodiment, $Cy^2$ is hydrogen, phenyl, thienyl, pyridyl, N-oxo-pyridyl, cyclopropyl, piperidinyl or piperazinyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonyl-aminomethyl or tetrazolyl. In yet another embodiment and $Cy^2$ is optionally substituted phenyl or optionally substituted pyridyl. Alternatively, $Cy^2$ is optionally substituted phenyl. In another embodiment, $Cy^2$ is phenyl substituted with 1 to 4 groups independently selected from chlorine or fluorine. Alternatively, $Cy^2$ is difluorophenyl. In another embodiment, $Cy^2$ is hydrogen. In another embodiment, $Cy^2$ is cyclopropyl.

$R^{1a}$ and $R^{1b}$ are each independently selected from (a) hydrogen or (b) ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl which are optionally substituted with up to three groups independently selected from fluorine, hydroxy, ($C_1$-$C_3$)alkoxy and $H_2NC(=O)$. In another embodiment, $R^{1a}$ and $R^{1b}$ are each independently H or ($C_1$-$C_6$)alkyl. In yet another embodiment $R^{1a}$ and $R^{1b}$ are each independently H, methyl, or ethyl. In another embodiment, $R^{1a}$ is methyl or ethyl. In yet another embodiment $R^{1a}$ is methyl. In another embodiment, $R^{1b}$ is methyl or hydrogen. Alternatively, $R^{1b}$ is hydrogen.

A is straight or branched ($C_1$-$C_6$)alkyl, ($C_2$-$C_8$)alkenyl or ($C_2$-$C_8$)alkynyl, optionally substituted with up to 4 groups independently selected from fluorine, cyano, oxo, $R^4$, —OH $R^{40}$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4SO_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo). In another embodiment, A is hydroxy($C_1$-$C_6$)alkyl or ($C_1$-$C_2$) alkoxy ($C_1$-$C_6$)alkyl. In another embodiment, A is ($C_1$-$C_4$)alkylcarbonylamino($C_1$-$C_4$)alkyl. In yet another embodiment, A is mono($C_1$-$C_2$)alkylaminocarbonyl($C_1$-$C_4$)alkyl or di($C_1$-$C_2$) alkylaminocarbonyl($C_1$-$C_4$)alkyl. Alternatively, A is 2-pyrimidinyl-amino($C_1$-$C_6$)alkyl; 2-pyridyl-amino($C_1$-$C_6$)alkyl; mono($C_1$-$C_2$)alkylamino($C_1$-$C_4$)alkyl or di($C_1$-$C_2$)alkylamino($C_1$-$C_4$)alkyl, wherein the pyrimidinyl and pyridyl are each optionally substituted with methyl or ethyl. Alternatively, A is ($C_1$-$C_6$)alkyl, optionally substituted with halogen. In another embodiment, A is ($C_1$-$C_4$)alkylsulfonyl($C_1$-$C_4$) alkyl. In another embodiment, A is ($C_1$-$C_4$)alkylsulfonylamino($C_1$-$C_4$)alkyl. In another embodiment, A is ($C_1$-$C_4$) alkoxyalkylamino($C_1$-$C_4$)alkyl. Alternatively, A is mono($C_1$-$C_4$)alkylaminocarbonyl($C_1$-$C_4$)alkyl or di($C_1$-$C_4$) alkylaminocarbonyl($C_1$-$C_4$)alkyl. Alternatively, A is methyl, ethyl, isopropyl or t-butyl. Alternatively, A is methyl or t-butyl.

t is 1, 2 or 3. Alternatively, t is 1 or 2. Alternatively, t is 1. Alternatively, t is 2.

Y is $(C_1-C_6)$alkyl or halo$(C_1-C_6)$alkyl.

n is 0, 1 or 2. Alternatively, n is 0.

E is (a) a bond or (b) $(C_1-C_3)$alkylene or $(C_1-C_2)$alkylenyloxy, wherein the 0 is attached to $R^2$, each of which is optionally substituted with 1 to 4 groups independently selected from methyl, ethyl, trifluoromethyl or oxo. Alternatively, E is a bond or $(C_1-C_3)$alkylene, optionally substituted with 1 to 4 groups independently selected from methyl, ethyl, trifluoromethyl or oxo. Alternatively, E is a bond or $CH_2$. Alternatively, E is a bond.

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, nitro, hydroxy, $(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl; wherein the 1 to 4 substituents for the group represented by $R^2$ are additionally selected from: amino, cyano, carboxy, $(C_1-C_6)$alkoxycarbonyl and hydroxy$(C_1-C_6)$alkyl, when E is bond or $(C_1-C_3)$alkylene, t is 1 and Q is O or $CH_2$, provided that $ER^2$ is not $CH_2Cl$, $CH_2OH$, $CHO$ or $CH_2O$ phenyl. In another embodiment, $R^2$ is optionally substituted aryl, optionally substituted heteroaryl or optionally substituted cycloalkyl. In another embodiment, $R^2$ is phenyl, thienyl or pyridyl each optionally substituted with halo or methyl. In another embodiment, $R^2$ is optionally substituted phenyl, optionally substituted thienyl or optionally substituted pyridyl. In another embodiment, $R^2$ is phenyl or pyridyl optionally substituted with one group selected from halo, methyl, methylthio or (4-morpholino) methyl. In yet another embodiment $R^2$ is optionally substituted phenyl or 4-fluorophenyl. In yet another embodiment $R^2$ is optionally substituted phenyl. Alternatively, $R^2$ is fluorophenyl. In another alternative $R^2$ is not alkyl, pyridinyl, cycloalkyl, cycloalkylalkyl, haloalkyl; unsubstituted phenyl, phenyl substituted with one to three substituents independently selected from fluoro, chloro, bromo, haloalkyl, alkoxy, hydroxy, haloalkyl and haloalkoxy, phenylalkyl or pyridinylalkyl, wherein phenylalkyl and pyridinylalkyl are optionally subtituted with one to three substituents independently selected from alkyl, halogen, haloalkyl and hydroxy, oxetane or oxetane substituted with alkyl, phenylalkoxyalkyl or phenylalkoxyalkyl substituted with one to three substituents independently selected from alkyl and halogen, hydroxyalkyl, pyridinyloxyalkyl or pyridinyloxyalkyl substituted with cyano.

Q is O, $NR^5$ or $CH_2$. In another embodiment, Q is $CH_2$ In another embodiment, Q is O. In yet another embodiment Q is $NR^5$.

each $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl; and each $R^5$ is independently H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

Another embodiment is a compound of Structural Formula $I_1$:

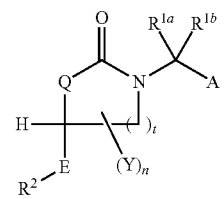

and wherein values and alternative values for Q, $R^2$, E, A, $R^{1a}$, $R^{1b}$, Y, n and t are as defined for Formula I above or a pharmaceutically acceptable salt, enantiomer or diastereomer thereof.

Another embodiment is a compound of Structural Formula $I_2$:

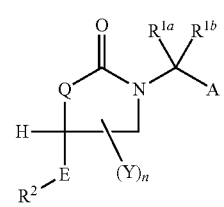

and wherein values and alternative values for Q, $R^2$, E, A, $R^{1a}$, $R^{1b}$, Y and n are as defined for Formula I above or a pharmaceutically acceptable salt, enantiomer or diastereomer thereof.

Another embodiment is a compound of Structural Formula $I_3$:

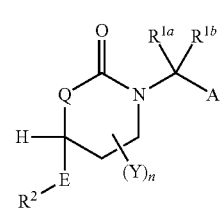

and wherein values and alternative values for Q, $R^2$, E, A, $R^{1a}$, $R^{1b}$, Y and n are as defined for Formula I above or a pharmaceutically acceptable salt, enantiomer or diastereomer thereof.

Another embodiment is a compound of Structural Formula I$_4$:

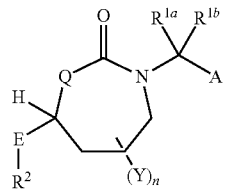

I$_4$ and wherein values and alternative values for Q, R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_5$:

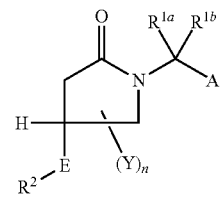

I$_5$ and wherein values and alternative values for R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_6$:

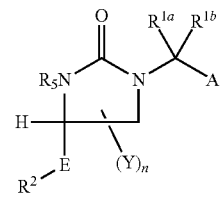

I$_6$ and wherein values and alternative values for R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_7$:

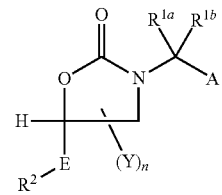

I$_7$ and wherein values and alternative values for R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_8$:

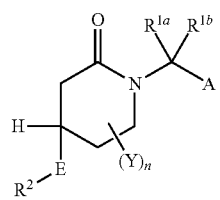

I$_8$ and wherein values and alternative values for R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_9$:

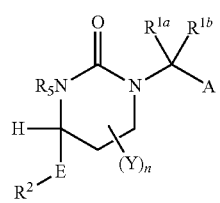

I$_9$ and wherein values and alternative values for R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_{10}$:

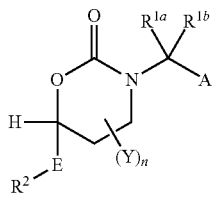

I$_{10}$ and wherein values and alternative values for R$^2$, E, A, R$^{1a}$, R$^{1b}$, Y and n are as defined for Formula I above or a pharmaceutically acceptable salt, enantiomer or diastereomer thereof.

Another embodiment is a compound of Structural Formula I$_{11}$:

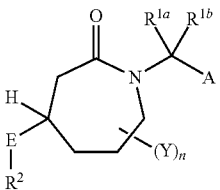

I$_{11}$ and wherein values and alternative values for $R^2$, E, A, $R^{1a}$, $R^{1b}$, Y and n are as defined for Formula I above or a pharmaceutically acceptable salt, enantiomer or diastereomer thereof.

Another embodiment is a compound of Structural Formula $I_{12}$:

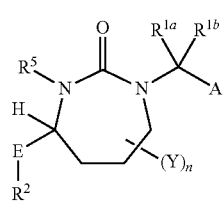

and wherein values and alternative values for $R^2$, E, A, $R^{1a}$, $R^{1b}$, Y and n are as defined for Formula I above or a pharmaceutically acceptable salt, enantiomer or diastereomer thereof.

Another embodiment is a compound of Structural Formula $I_{13}$:

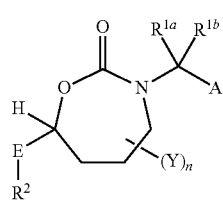

and wherein values and alternative values for $R^2$, E, A, $R^{1a}$, $R^{1b}$, Y and n are as defined for Formula I above or a pharmaceutically acceptable salt, enantiomer or diastereomer thereof.

Another embodiment is a compound of Structural Formula $I_{14}$:

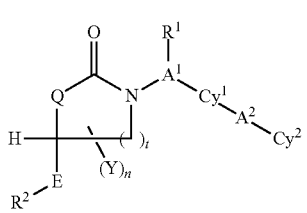

and wherein values and alternative values for Q, $R^2$, E, $A^1$, $R^1$, $Cy^1$, $Cy^2$, Y, n and t are as defined for Formula I above or a pharmaceutically acceptable salt, enantiomer or diastereomer thereof.

Another embodiment is a compound of Structural Formula $I_{15}$:

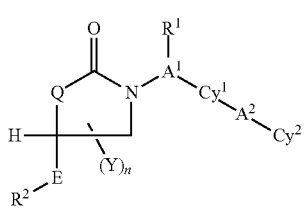

and wherein values and alternative values for Q, $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{16}$:

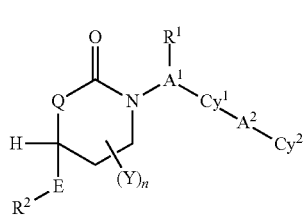

and wherein values and alternative values for Q, $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{17}$:

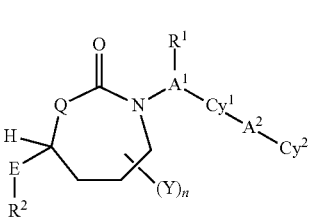

and wherein values and alternative values for Q, $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{18}$:

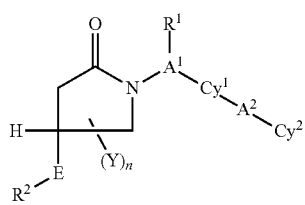

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{19}$:

Another embodiment is a compound of Structural Formula $I_{19}$:

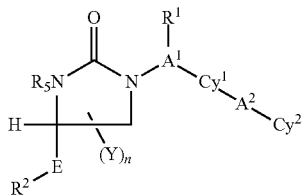

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{20}$:

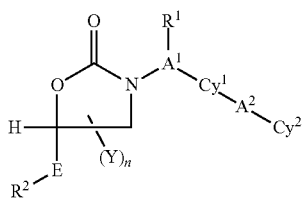

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{21}$:

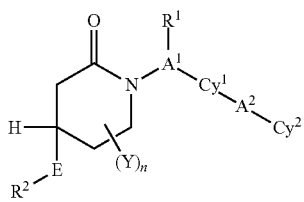

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{22}$:

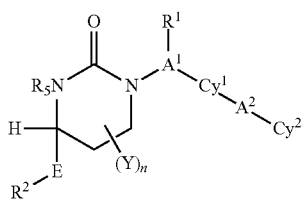

and wherein values and alternative values for $R^2$, E, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{23}$:

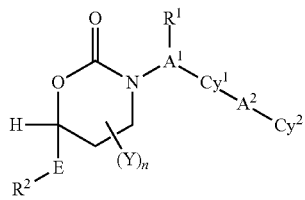

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{24}$:

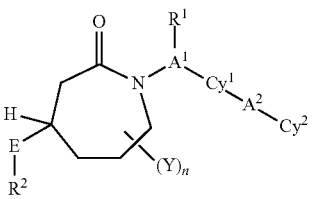

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{25}$:

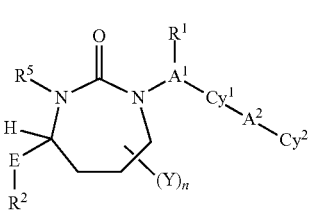

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $I_{26}$:

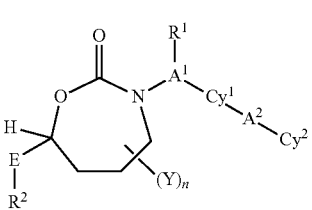

and wherein values and alternative values for $R^2$, E, $A^1$, $R^1$, $Cy^1$, $A^2$, $Cy^2$, Y and n are as defined for Formula I above or a pharmaceutically acceptable salt, enantiomer or diastereomer thereof.

Another embodiment is a compound of Structural Formula $Ia_1$:

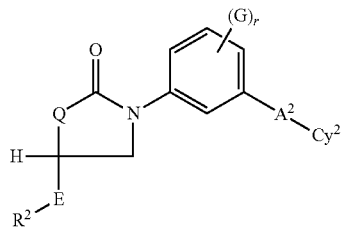

Ia₁ and wherein values and alternative values for Q, $R^2$, E, $A^2$ and $Cy^2$ are as defined for Formula I above, r is 0, 1, 2, 3 or 4 and G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxyl or $(C_1-C_6)$alkylcarbonyl;

or a pharmaceutically acceptable salt, enantiomer or diastereomer thereof.

Another embodiment is a compound of Structural Formula $Ia_2$:

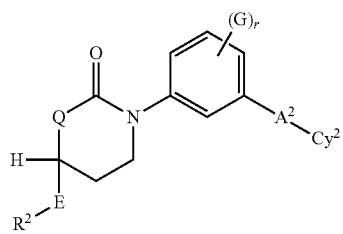

Ia₂ and wherein values and alternative values for Q, $R^2$, E, $A^2$ and $Cy^2$ are as defined for Formula I above, G and r are as defined for Formula Ia, above, or a pharmaceutically acceptable salt, enantiomer or diastereomer thereof.

Another embodiment is a compound of Structural Formula $Ia_3$:

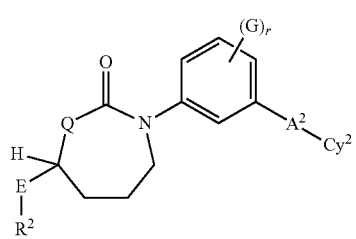

Ia₃ and wherein values and alternative values for Q, $R^2$, E, $A^2$ and $Cy^2$ are as defined for Formula I above, G and r are as defined for Formula Ia, above, or a pharmaceutically acceptable salt, enantiomer or diastereomer thereof.

Another embodiment is a compound of Structural Formula $Ib_1$:

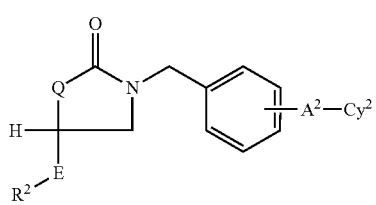

Ib₁ and wherein values and alternative values for Q, $R^2$, E, $A^2$ and $Cy^2$ are as defined for Formula I above, or a pharmaceutically acceptable salt, enantiomer or diastereomer thereof.

Another embodiment is a compound of Structural Formula $Ib_2$:

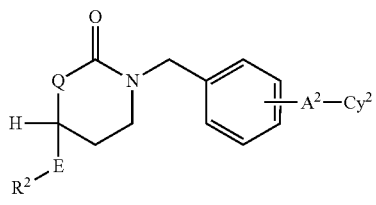

Ib₂ and wherein values and alternative values for Q, $R^2$, E, $A^2$ and $Cy^2$ are as defined for Formula I above, or a pharmaceutically acceptable salt, enantiomer or diastereomer thereof.

Another embodiment is a compound of Structural Formula Ib₃:

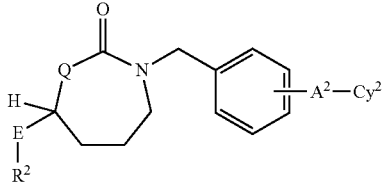

and wherein values and alternative values for Q, R², E, A² and Cy² are as defined for Formula I above, or a pharmaceutically acceptable salt, enantiomer or diastereomer thereof.

Another embodiment is a compound of Structural Formula Ic₁:

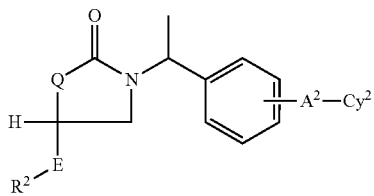

and wherein values and alternative values for Q, R², E, A² and Cy² are as defined for Formula I above, or a pharmaceutically acceptable salt, enantiomer or diastereomer thereof.

Another embodiment is a compound of Structural Formula Ic₂:

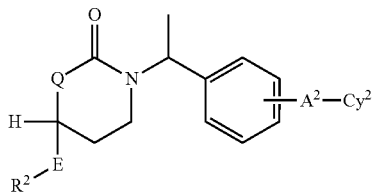

and wherein values and alternative values for Q, R², E, A² and Cy² are as defined for Formula I above, or a pharmaceutically acceptable salt, enantiomer or diastereomer thereof.

Another embodiment is a compound of Structural Formula Ic₃:

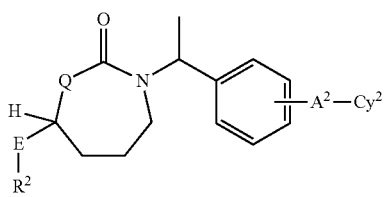

and wherein values and alternative values for Q, R², E, A² and Cy² are as defined for Formula I above, or a pharmaceutically acceptable salt, enantiomer or diastereomer thereof.

Another embodiment is a compound of Structural Formula Id₁:

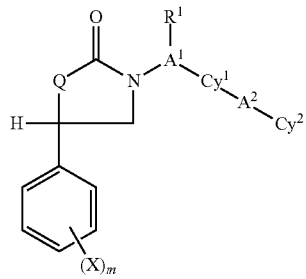

and wherein values and alternative values for Q, R¹, A¹, Cy¹, A² and Cy² are as defined for Formula I above, m is 0, 1, 2, 3 or 4 and X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkyl-alkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

or a pharmaceutically acceptable salt, enantiomer or diastereomer thereof.

Another embodiment is a compound of Structural Formula Id₂:

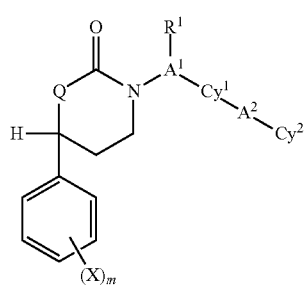

and wherein values and alternative values for Q, $A^1$, $Cy^1$, $A^2$ and $Cy^2$ are as defined for Formula I above, X and m are as defined for Formula $Id_1$ above, or a pharmaceutically acceptable salt, enantiomer or diastereomer thereof.

Another embodiment is a compound of Structural Formula $Id_3$:

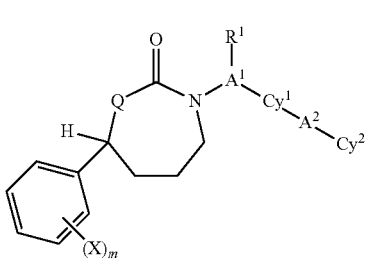

$Id_3$ and wherein values and alternative values for Q, $R^1$, $A^1$, $Cy^1$, $A^2$ and $Cy^2$ are as defined for Formula I above, X and m are as defined for Formula $Id_1$ above, or a pharmaceutically acceptable salt, enantiomer or diastereomer thereof.

Another embodiment is a compound of Structural Formula $Ie_1$:

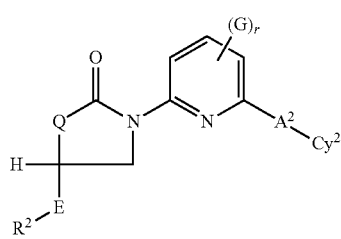

$Ie_1$ and wherein values and alternative values for Q, $R^2$, E, $A^2$ and $Cy^2$ are as defined for Formula I above,
r is 0, 1, 2, 3 or 4 and
G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkyl-alkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl, or a pharmaceutically acceptable salt, enantiomer or diastereomer thereof.

Another embodiment is a compound of Structural Formula $Ie_2$:

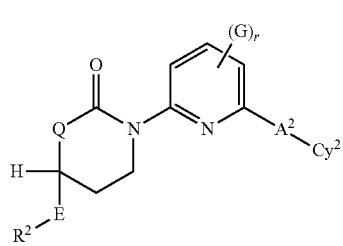

$Ie_2$ and wherein values and alternative values for Q, $R^2$, E, $A^2$ and $Cy^2$ are as defined for Formula I above, G and r are as defined for Formula $Ie_1$ above, or a pharmaceutically acceptable salt, enantiomer or diastereomer thereof.

Another embodiment is a compound of Structural Formula $Ie_3$:

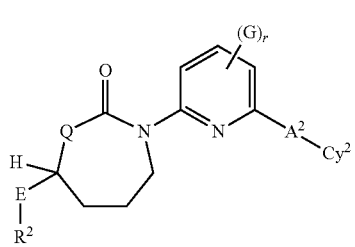

$Ie_3$ and wherein values and alternative values for Q, $R^2$, E, $A^2$ and $Cy^2$ are as defined for Formula I above, G and r are as defined for Formula Ie, above, or a pharmaceutically acceptable salt, enantiomer or diastereomer thereof.

Another embodiment is a compound of Structural Formula $If_1$:

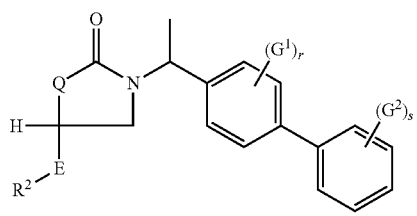

$If_1$ and wherein values and alternative values for Q, $R^2$ and E are as defined for Formula I above,
r and s are independently 0, 1, 2, 3 or 4 and
$G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo (C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkyl-alkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkanesulfinyl, halo (C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo (C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo (C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆) alkyl, hydroxy(C₁-C₆)alkoxy, heteroaryl, amino(C₁-C₆)alkyl, (C₁-C₆)alkylamino(C₁-C₆)alkyl, di(C₁-C₆)alkylamino (C₁-C₆)alkyl amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl, or a pharmaceutically acceptable salt, enantiomer or diastereomer thereof.

Another embodiment is a compound of Structural Formula If₂:

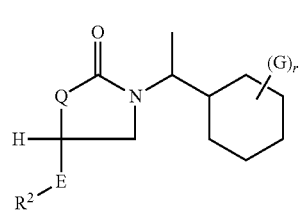

If₂ and wherein values and alternative values for Q, R² and E are as defined for Formula I above, G¹, G², r and s are as defined for Formula If₁ above, or a pharmaceutically acceptable salt, enantiomer or diastereomer thereof.

Another embodiment is a compound of Structural Formula If₃:

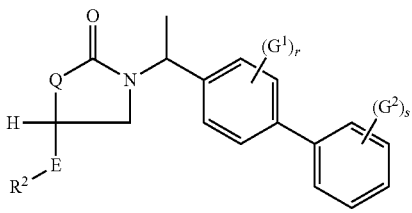

If₃ and wherein values and alternative values for Q, R² and E are as defined for Formula I above, G¹, G², r and s are as defined for Formula If₁ above, or a pharmaceutically acceptable salt, enantiomer or diastereomer thereof.

Another embodiment is a compound of Structural Formula Ig₁:

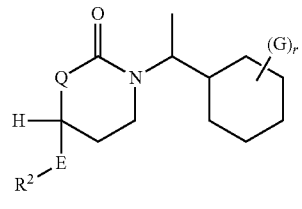

Ig₁ and wherein values and alternative values for Q, R² and E are as defined for Formula I above,
r is 0, 1, 2, 3 or 4 and
G is independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo (C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo (C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo (C₁-C₆)alkoxy, halo(C₃-C₆)cycloalkoxy, halo(C₄-C₇)cycloalkylalkoxy, (C₁-C₆)alkylthio, (C₃-C₆)cycloalkylhio, (C₄-C₇)cycloalkyl-alkylthio, halo(C₁-C₆)alkylthio, halo(C₃-C₆)cycloalkylhio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkanesulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo (C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo (C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆) alkyl, hydroxy(C₁-C₆)alkoxy, heteroaryl, amino(C₁-C₆)alkyl, (C₁-C₆)alkylamino(C₁-C₆)alkyl, di(C₁-C₆)alkylamino (C₁-C₆)alkyl amino(C₂-C₆)alkoxy, (C₁-C₆)alkylamino(C₂-C₆)alkoxy, di(C₁-C₆)alkylamino(C₂-C₆)alkoxyl and (C₁-C₆)alkylcarbonyl, or a pharmaceutically acceptable salt, enantiomer or diastereomer thereof.

Another embodiment is a compound of Structural Formula Ig₂:

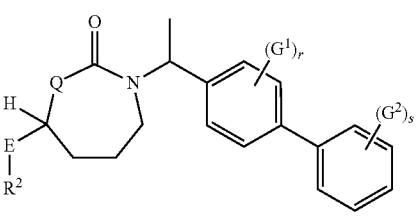

Ig₂ and wherein values and alternative values for Q, R² and E are as defined for Formula I above, G and r are as defined for Formula Ig₁ above, or a pharmaceutically acceptable salt, enantiomer or diastereomer thereof.

Another embodiment is a compound of Structural Formula Ig$_3$:

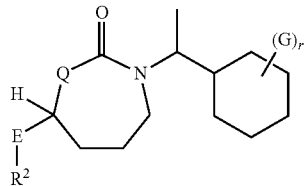

Ig$_3$ and wherein values and alternative values for Q, R$^2$ and E are as defined for Formula I above, G and r are as defined for Formula Ig$_1$ above, or a pharmaceutically acceptable salt, enantiomer or diastereomer thereof.

Another embodiment is a compound of Structural Formula Ih$_1$:

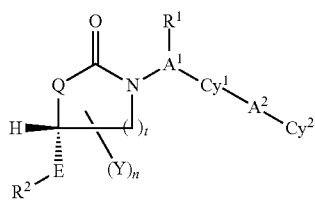

Ih$_1$ and wherein values and alternative values for Q, R$^2$, E, A$^1$, R$^1$, Cy$^1$, A$^2$, Cy$^2$, Y n and t are as defined for Formula I above, or a pharmaceutically acceptable salt, enantiomer or diastereomer thereof.

Another embodiment is a compound of Structural Formula Ih$_2$:

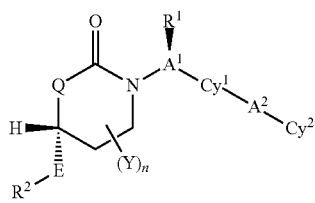

Ih$_2$ and wherein values and alternative values for Q, R$^2$, E, A$^1$, R$^1$, Cy$^1$, A$^2$, Cy$^2$, Y, n and t are as defined for Formula I above, or a pharmaceutically acceptable salt, enantiomer or diastereomer thereof.

Another embodiment is a compound of Structural Formula Ih$_3$:

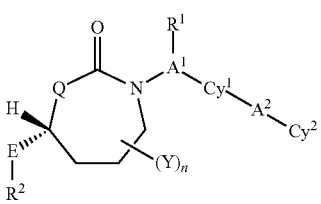

Ih$_3$ and wherein values and alternative values for Q, R$^2$, E, A$^1$, R$^1$, Cy$^1$, A$^2$, Cy$^2$, Y, n and t are as defined for Formula I above, or a pharmaceutically acceptable salt, enantiomer or diastereomer thereof.

Another embodiment is a compound of Structural Formula Ii$_1$:

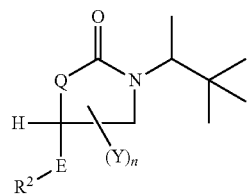

Ii$_1$ and wherein values and alternative values for Q, R$^2$, E, Y and n are as defined for Formula I above, or a pharmaceutically acceptable salt, enantiomer or diastereomer thereof.

Another embodiment is a compound of Structural Formula Ii$_2$:

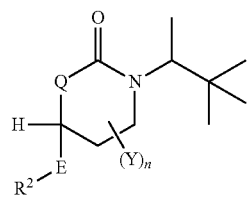

Ii$_2$ and wherein values and alternative values for Q, R$^2$, E, Y and n are as defined for Formula I above, or a pharmaceutically acceptable salt, enantiomer or diastereomer thereof.

Another embodiment is a compound of Structural Formula Ii$_3$:

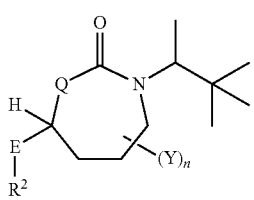

Ii$_3$ and wherein values and alternative values for Q, R$^2$, E, Y and n are as defined for Formula I above, or a pharmaceutically acceptable salt, enantiomer or diastereomer thereof.

Another embodiment is a compound of Structural Formula Ij$_1$:

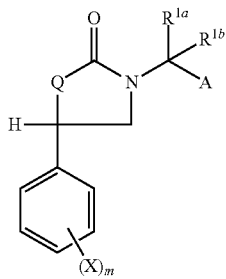

and wherein values and alternative values for Q, $R^{1a}$, $R^{1b}$ and A are as defined for Formula I above, X and m are as defined for Formula $Id_1$ above, or a pharmaceutically acceptable salt, enantiomer or diastereomer thereof.

Another embodiment is a compound of Structural Formula $Ij_2$:

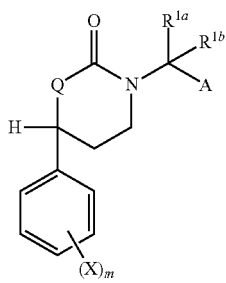

and wherein values and alternative values for Q, $R^{1a}$, $R^{1b}$ and A are as defined for Formula I above, X and m are as defined for Formula $Id_1$ above, or a pharmaceutically acceptable salt, enantiomer or diastereomer thereof.

Another embodiment is a compound of Structural Formula $Ij_3$:

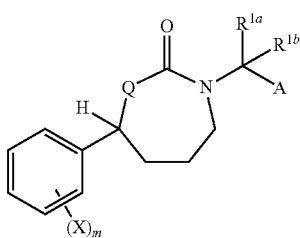

and wherein values and alternative values for Q, $R^{1a}$, $R^{1b}$ and A are as defined for Formula I above, X and m are as defined for Formula $Id_1$ above, or a pharmaceutically acceptable salt, enantiomer or diastereomer thereof.

In another embodiment of the invention, values for variables in Structural Formula I or any of Structural Formulas $I_{14}$-$I_{26}$ or $Ia_{1-3}$-$Ih_{1-3}$ are:

R is

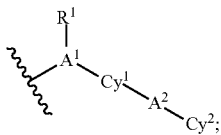

$R^1$ is absent or is methyl or ethyl;
$A^1$ is a bond or $CH_2$;
$Cy^1$ is phenyl, cyclohexyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy and 2-hydroxy-2-methylpropoxy;
$A^2$ is a bond, O or $OCH_2CO$;
$Cy^2$ is (a) hydrogen or (b) phenyl, thienyl, pyridyl, N-oxo-pyridyl, cyclopropyl, piperidinyl or piperazinyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonyl-aminomethyl or tetrazolyl;
n is 0;
t is 1, 2 or 3;
Q is O, $NR^5$ or $CH_2$;
E is a bond or $CH_2$;
$R^2$ is phenyl or pyridyl optionally substituted with one group selected from halo, methyl, methylthio or (4-morpholino) methyl.

In another embodiment of the invention, values for variable in the Structural

Formula I or any of the formulas $I_1$-$I_{13}$ or $Ij_{1-3}$ are:
R is

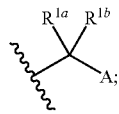

$R^{1a}$ is methyl or ethyl;
$R^{1b}$ is methyl or hydrogen;
A is methyl, ethyl, isopropyl or t-butyl;
n is 0;
t is 1, 2 or 3;
Q is O, $NR^5$ or $CH_2$;
E is a bond or $CH_2$; and
$R^2$ is phenyl, thienyl or pyridyl each optionally substituted with halo or methyl.

Definitions

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo [2.2.2]octyl, bicyclo[2.2.1]heptyl, Spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. A heterocyclyl can be optionally substituted with 1-4 substituents. Exemplary substituents include alkyl, haloalkyl and oxo.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed comopounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R" and "S" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

The following abbreviations have the indicated meanings:

| Abbreviation | Meaning |
|---|---|
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC.HCl, EDCl | 1-[3-(dimethylamino)propyl]-3-ethylcarbodiimide hydrochloride |
| Equiv | equivalents |
| EtOAc | ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | 3-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |

-continued

| Abbreviation | Meaning |
|---|---|
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthetic Methods

Compounds of Formula I can be prepared by several processes. In the discussion below, A, A$^1$, A$^2$, Cy$^1$, E, R$^1$, R$^2$, R$^5$, R$^{1a}$, R$^{1b}$, Y, n and t have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion.

This is especially the case when the excess reagent can be readily removed by evaporation or extraction. Bases employed to neutralize HCl in reaction mixtures are generally used in slight to substantial excess (1.05-5 equivalents).

In a first process compounds of Formula I, wherein t is 2, n is 0 and Q is CH$_2$, are prepared by ring closure of intermediates of Formula II wherein Z$^a$ is a leaving group such as halide, alkanesulfonate, haloalkanesulfonate or arylsulfonate, using a base such as NaH.

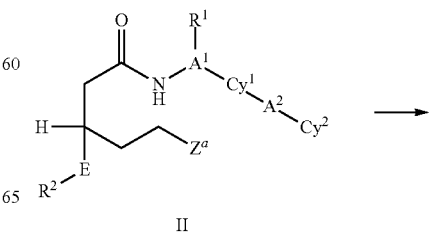

II

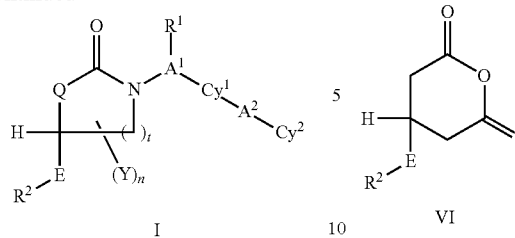

I

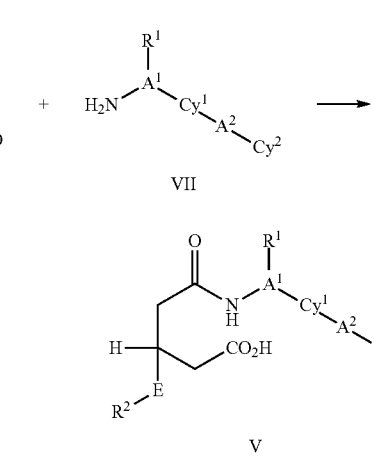

Intermediates of Formula II, wherein $Z^a$ is alkanesulfonate, haloalkanesulfonate or arylsulfonate, can be prepared from alchols of Formula III and sulfonyl chlorides of Formula IV ($Z^a$=Cl) or sulfonic anhydrides of Formula IV ($Z^a$=$R^aSO_2O$—), wherein $R^a$ is alkyl, haloalkyl or aryl.

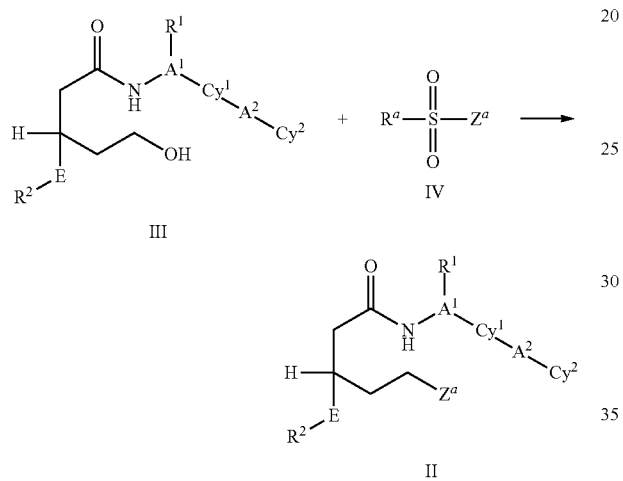

Alcohols of Formula III can be prepared by reduction of carboxylic acids of Formula V using, for example, borane in THF.

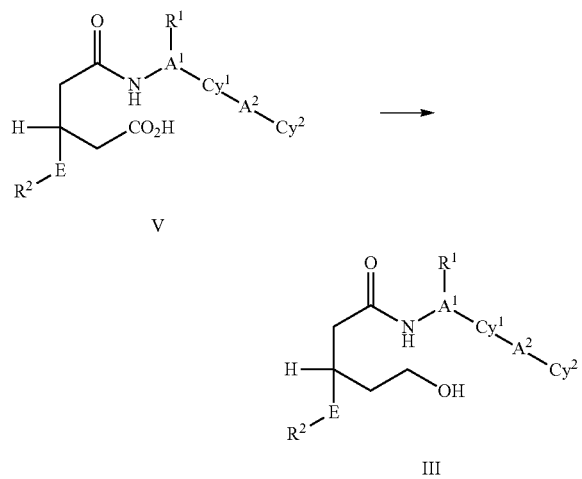

Carboxylic acids of Formula V can be prepared by reaction of cyclic anhydrides of Formula VI with amines of Formula VII.

Cyclic anhydrides of Formula VI can be prepared from diacids of Formula VIII by treatment with acetic or trifluoroacetic anhydride.

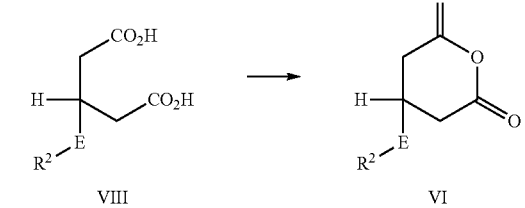

Diacids of Formula VIII can be prepared from aldehydes of Formula IX and β-ketoesters of Formula X, wherein $R^b$ is lower alkyl, by reaction with piperidine under Knoevenagel conditions, followed by treatment with NaOH and with HCl.

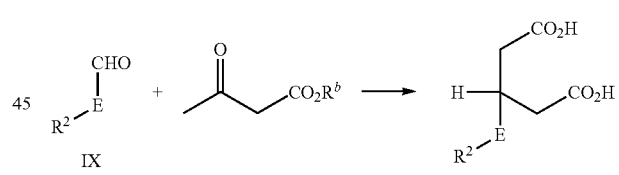

Amine intermediates of Formula VII, wherein $A^1$=$CH_2$ and $R^1$ is absent, can be prepared by reduction of amides of Formula XI using a hydride reagent such as $BH_3$·THF solution, $BH_3$·$Me_2S$ or $LiAlH_4$ in an ethereal solvent such as THF or DME at 20° C. to 100° C. for between 1 h and 48 h:

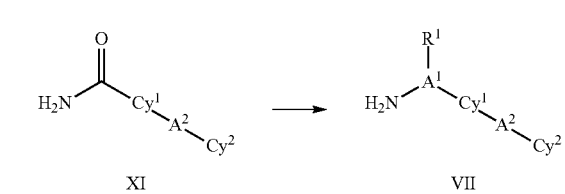

Amine intermediates of Formula VII, wherein $A^1$ is a bond, $R^1$ is absent and $Cy^1$ is not an aromatic or heteroaromatic ring, can be prepared from ketones of formula XII via oximes of Formula XIII or by reductive amination of ketones of Formula XII with ammonia:

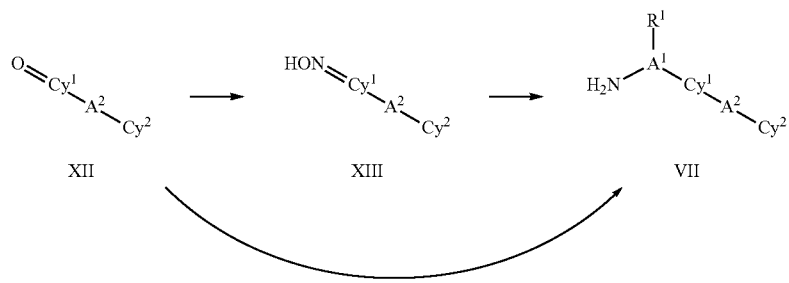

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th) Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Amine intermediates of Formula VII, wherein $A^1$ is CH, can be prepared from ketones of Formula XIV by reductive amination with ammonia.

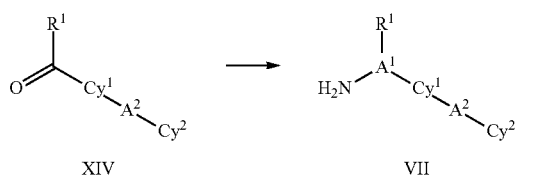

Amine intermediates of Formula VII, wherein $A^1$ is CH, can be prepared from alcohols of Formula XV via azides of Formula XVI. The conversion of alcohols of Formula XV to azides of Formula XVI can be accomplished with, for example, diphenylphosphoryl azide. Reduction of azides of Formula XVI to amines of Formula VII can be effected, for example, by hydrogenation in the presence of a palladium catalyst or by reaction with triphenylphosphine in wet THF.

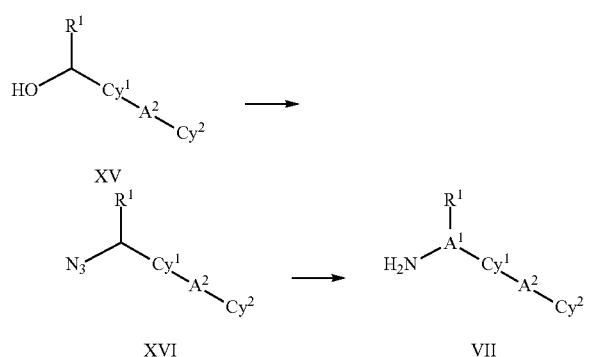

Amine intermediates of Formula VII, wherein $A^1$ is CH, can be prepared by reaction of sulfinyl imine intermediates of Formula XVII with organometallic reagents of Formula XVIII, wherein M is Li, MgCl, MgBr or MgI, followed by treatment with acid to remove the t-butylsulfinyl group.

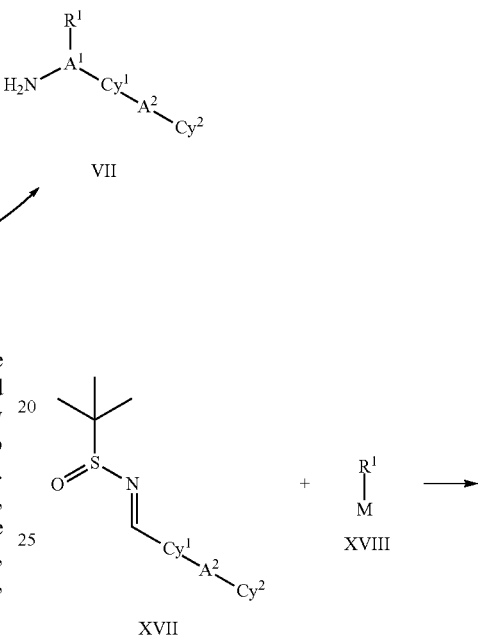

Sulfinyl imines of Formula XVII can be prepared by treatment of aldehyde intermediates of Formula XVIII with 2-methylpropane-2-sulfinamide.

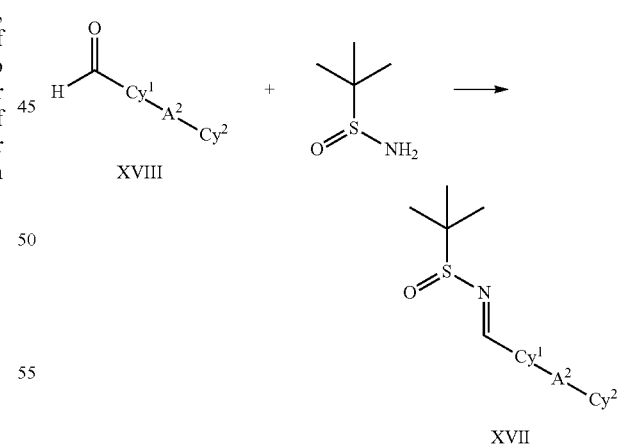

In a second process, compounds of Formula I, wherein Q is O or $NR^5$, can be prepared by reaction of aminoalcohols or diamines intermediate of Formula XIX with reagents of Formula XX, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

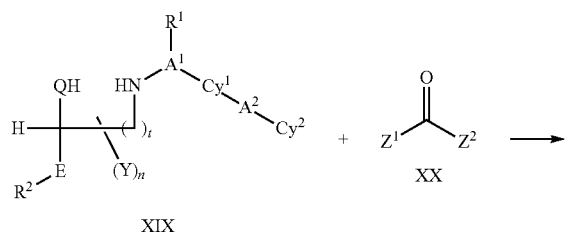

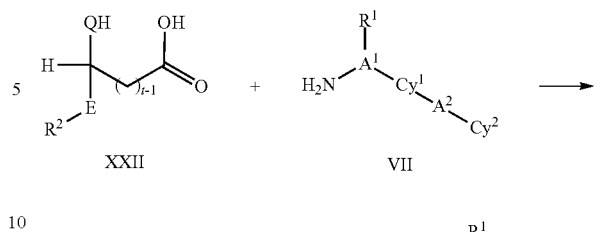

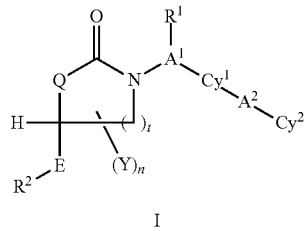

Certain instances of reagent XX are especially convenient because they are commercially available. For example when $Z^1$ and $Z^2$ are both chloride, XX is phosgene. When $Z^1$ and $Z^2$ are both 1-imidazolyl, XX is carbonyl diimidazole. When $Z^1$ is chloride and $Z^2$ is p-nitrophenoxide, XX is p-nitrophenyl chloroformate. When $Z^1$ and $Z^2$ are both $OCCl_3$, XX is triphosgene and as little as one third of molar equivalent can be used.

Aminoalcohol and diamine intermediates of Formula XIX, wherein n=0, can be prepared by reduction of amides of Formula XXI using a hydride reagent such as $BH_3$.THF solution, $BH_3.Me_2S$ or $LiAlH_4$ in an ethereal solvent such as THF or DME at 20° C. to 100° C. for between 1 h and 48 h:

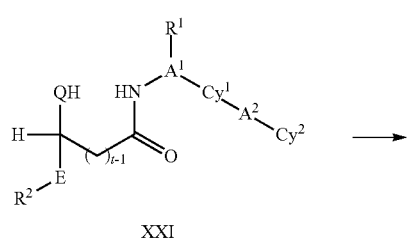

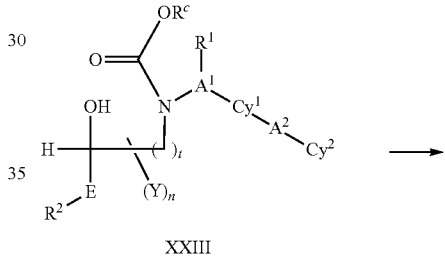

Intermediates of Formula XXI can be prepared by coupling of α-, β- or γ-hydroxyacids (Q=0) and α-, β- or γ-aminoacids (Q=$NR^5$) of Formula XXII with amines of Formula VII using standard peptide coupling reagents such as EDC in the presence of HOBt and N,N-diisopropylethylamine in an inert solvent such as $CH_2Cl_2$ at 0-30° C. for between 1 h and 24 h:

In a third process, compounds of Formula I, wherein Q is 0 and t is 1 or 2, can be prepared by reaction of hydroxycarbamates of Formula XXIII, wherein $R^c$ is an alkyl or arylalkyl group such as methyl, t-butyl or benzyl, with a strong base such as NaH.

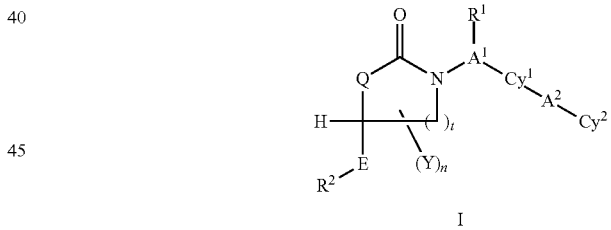

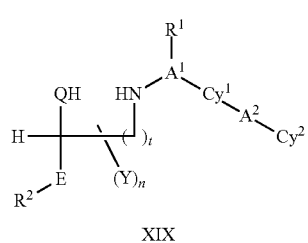

Hydroxycarbamates of Formula XXIII can be prepared by reduction of ketocarbamates of Formula XXIV with, for example, $NaBH_4$ in MeOH.

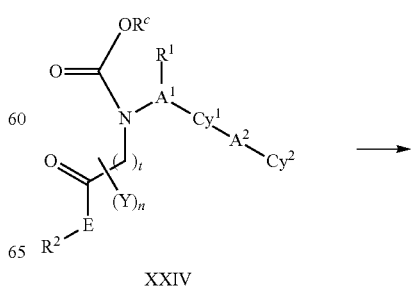

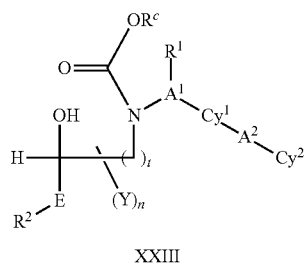

XXIII

Ketocarbamates of Formula XXIV can be prepared by reaction of β-aminoketones of Formula XXV with reagents of Formula XXVI, wherein $R^d$ is a leaving group such as chloride, succinyloxy, imidazolyl or t-butoxycarboxycarbonyl:

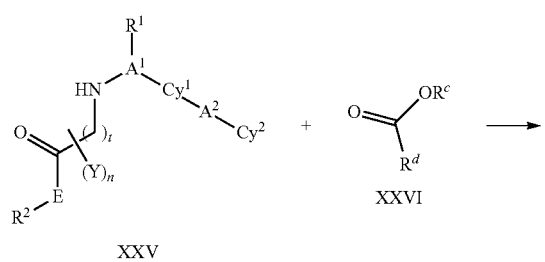

XXV  XXVI

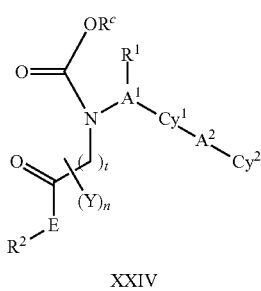

XXIV

β-Aminoketones of Formula XXV, wherein n=0 and t is 2, can be prepared by reaction of α,β-unsaturated ketones of Formula XXVII or β-chloroketones of Formula XXVIII with amines of Formula VII:

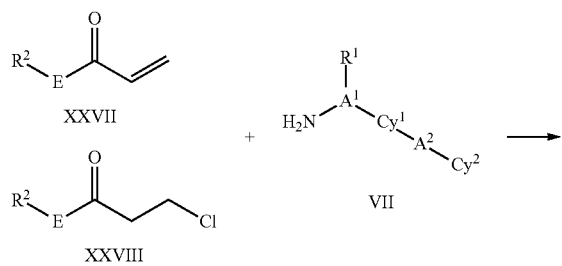

XXVII  XXVIII  VII

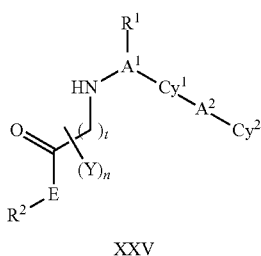

XXV

α-Aminoketones of Formula XXV, wherein n=0 and t is 1, can be prepared by reaction of α-haloketones of Formula XXIX, wherein $Z^3$ is Br or Cl, with amines of Formula VII:

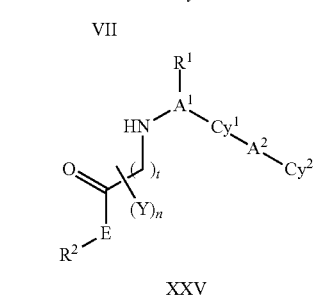

XXIX  VII

XXV

Hydroxycarbamates of Formula XXIII can also be prepared by addition of organometallic reagents of Formula XXX, wherein M is Li, MgCl, MgBr or MgI, to aldehydes of Formula XXXI.

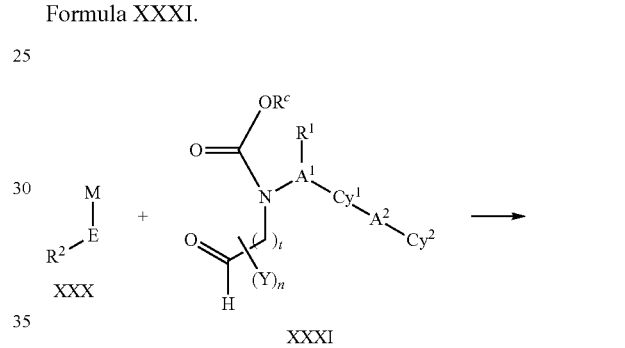

XXX  XXXI

XXIII

Aldehydes of Formula XXXI can be prepared by oxidation of alcohols of Formula XXXII with, for example, Dess-Martin periodinane. Alcohols of Formula XXXII can be prepared by reduction of esters of Formula XXXIII, wherein $R^d$ is alkyl or arylalkyl using for example LiAlH$_4$, or by reduction of acids of Formula XXXI, wherein $R^d$ is hydrogen, using for example isobutyl chloroformate and NaBH$_4$.

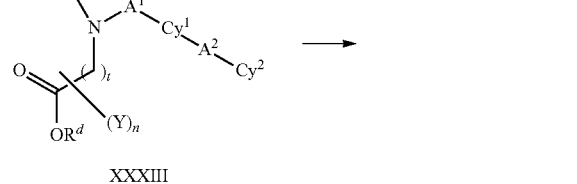

XXXIII

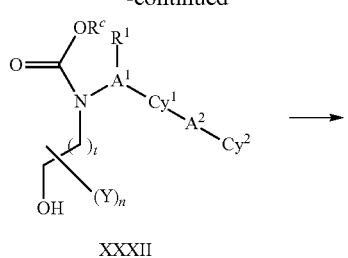

XXXII

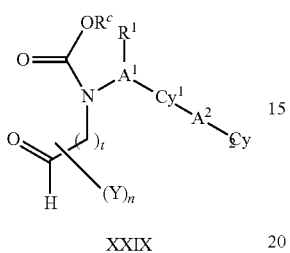

XXIX

Esters of Formula Formula XXXIII, wherein n is 0 and t is 1, can be prepared by alkylation of carbamates of Formula XXXIV with bromoacetic acid esters of Formula XXXV using a base such as NaH.

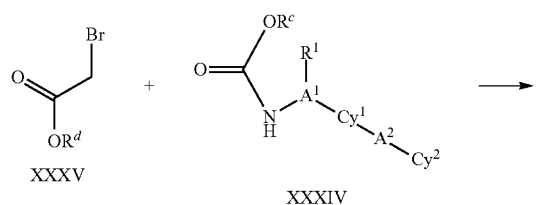

XXXV     XXXIV

-continued

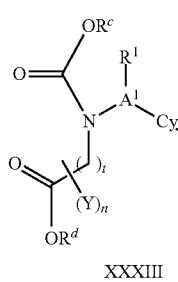

XXXIII

In a fourth process compounds of Formula I, wherein Q is O and t is 1 or 2, can be prepared by reaction of alcohols of Formula XXXVI, wherein $Z^4$ is halide, alkanesulfonate, haloalkanesulfonate or arylsulfonate, with isocyanates of Formula XXXVII in the presence of a base:

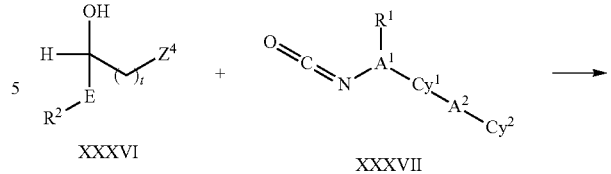

XXXVI     XXXVII

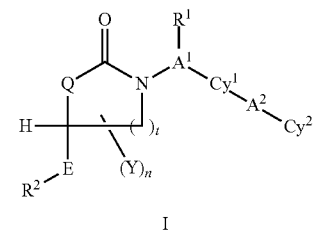

I

Isocyanates of Formula XXXVII can be prepared from amines of Formula VII by treatment with phosgene, diphosgene or triphosgene.

Alcohols of Formula XXXVI, wherein $Z^4$ is chloride and t is 2, can be prepared by reduction of β-haloketones of Formula XXVIII with hydride reagents such as $NaBH_4$. Similarly, alcohols of Formula XXXVI, wherein $Z^4$ is chloride or bromide and t is 1, can be prepared by reduction of α-haloketones of Formula XXIX, wherein $Z^3$ is chloride or bromide using a hydride reagent such as $NaBH_4$.

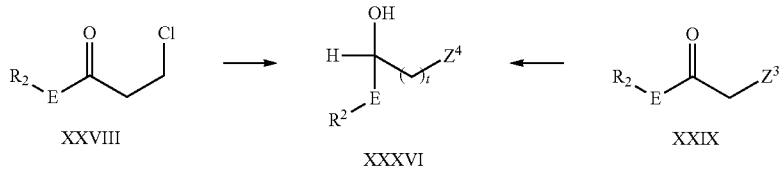

XXVIII         XXXVI         XXIX

In a fifth process compounds of Formula I, wherein $A^1$ is $CH_2$ and $R^1$ is absent, can be prepared by reaction of compounds of Formula XXXVII, with alkylating agents of Formula XXXVIII, wherein $Z^5$ is a leaving group such as Br, I, $OSO_2Me$, $OSO_2CF_3$ or $OSO_2Ph$, in the presence of a base such as NaH or $K_2CO_3$:

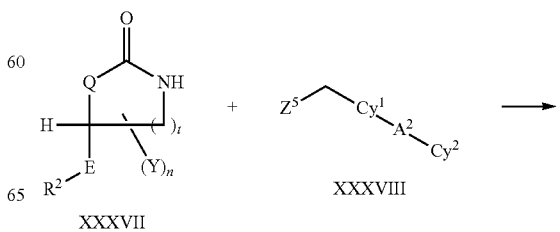

XXXVII         XXXVIII

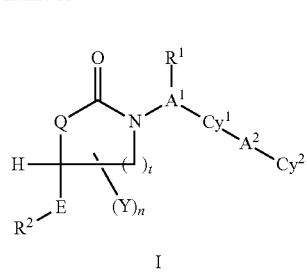

I

Compounds of Formula XXXVII, wherein Q=O or NR⁵, can be prepared by treatment of compounds of Formula XXXIX with various reagents of Formula XX, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at −10° C. to 120° C.:

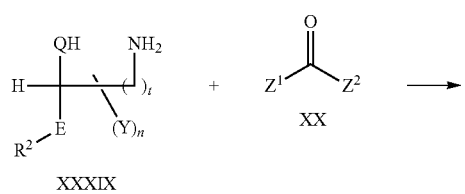

XXXIX          XX

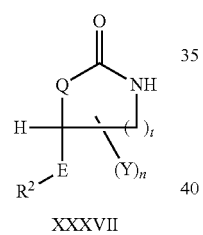

XXXVII

Compounds of Formula XXXVII, wherein Q is $CH_2$, can be prepared by ring expansion of ketones of Formula XL with hydrazoic acid under Schmidt reaction conditions.

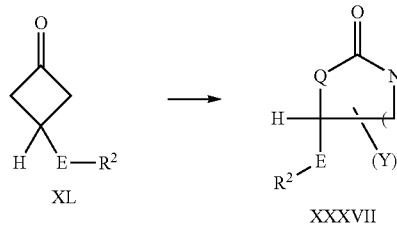

XL → XXXVII

In a sixth process compounds of Formula I, wherein A is a bond can be prepared by reaction of compounds of Formula XXXVII, with compounds of Formula XLI, wherein $Z^6$ is a leaving group such as chloro, bromo, iodo or $OSO_2CF_3$, in the presence of a base such as $K_2CO_3$ and a copper or palladium catalyst in an inert solvent such as dioxane, DMF or NMP at elevated temperature:

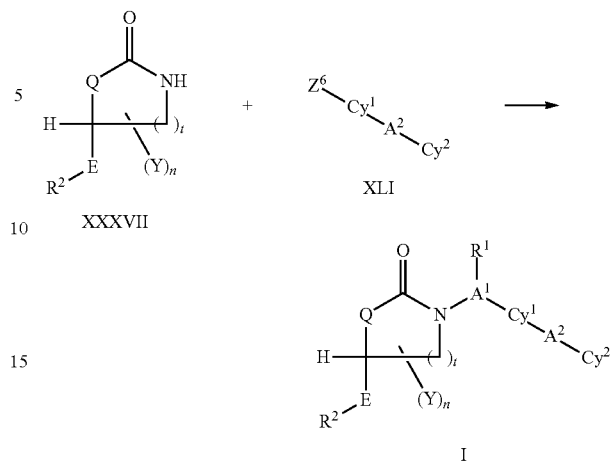

XXXVII + XLI →

I

In a seventh process, compounds of Formula I, wherein Q is $CH_2$ and $A^1$ is $CH_2$ and $R^1$ is absent, can be prepared by reaction of ketones of Formula XL with azides of Formula XLII in the presence of $TiCl_4$.

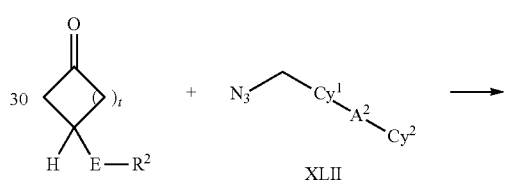

XLI + XLII →

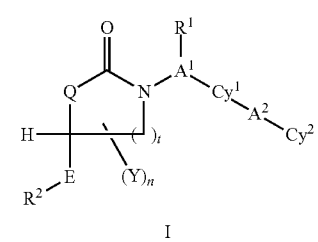

I

In an eighth process, compounds of Formula I, wherein Q is $CH_2$, are prepared by photolytic rearrangement of oxaziridines of Formula XLIII.

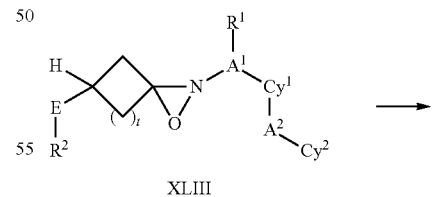

XLIII →

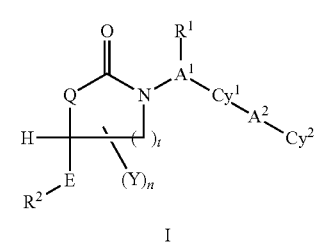

I

Oxaziridines of Formula XLIII can be prepared from ketones of Formula XL and amines of Formula VII to form imines of Formula XLIV, followed by oxidation with, for example, m-CPBA.

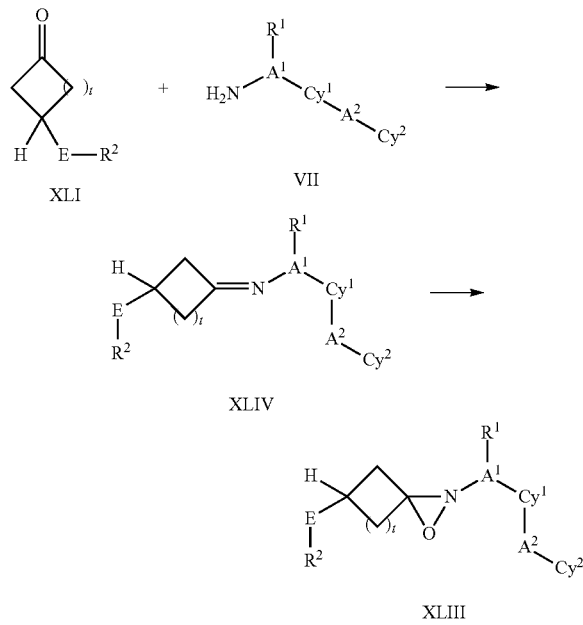

In a ninth process, compounds of Formula I can be prepared from other compounds of Formula I. For example:

(1) a compound of Formula I wherein $Cy^1$ is substituted with bromine or iodine, $A^2$ is a bond and $Cy^2$ is hydrogen can be reacted with an optionally substituted aryl or heteroarylboronic acid or ester in the presence of a palladium catalyst to give a compound of Formula I wherein $A^2$ is a bond and $Cy^2$ is optionally substituted aryl or heteroaryl.

(2) a compound of Formula I wherein $R^1$ is ω-hydroxy($C_2$-$C_6$)alkyl can be oxidized to a compound of Formula I wherein $R^1$ is ω-carboxy($C_1$-$C_6$)alkyl using Jones reagent.

(3) a compound of Formula I wherein $R^1$ is ω-carboxy($C_1$-$C_6$)alkyl can be coupled with ammonia or a ($C_1$-$C_6$)alkylamine using a standard peptide coupling reagent such as EDC to afford a compound of Formula I wherein $R^1$ is ω-$H_2$NC(=O)($C_1$-$C_6$)alkyl or ω-{($C_1$-$C_6$)alkylNHC(=O)}($C_1$-$C_6$)alkyl.

(4) a compound of Formula I wherein $R^1$ is ω-hydroxy($C_1$-$C_6$)alkyl can be converted to its methanesulfonate or trifluoromethanesulfonate, treated with sodium azide and reduced to give a compound of Formula I, wherein $R^1$ is ω-amino($C_1$-$C_6$)alkyl.

(5) a compound of Formula I wherein $R^1$ is amino($C_1$-$C_6$)alkyl can be reacted with acetic anhydride or acetyl chloride to give a compound of Formula I wherein $R^1$ is {acetylamino}($C_1$-$C_6$)alkyl.

(6) a compound of Formula I wherein $R^1$ is amino($C_1$-$C_6$)alkyl can be reacted with methanesulfonyl chloride to give a compound of Formula I wherein $R^1$ is {methanesulfonylamino}($C_1$-$C_6$)alkyl.

(7) a compound of Formula I, wherein $R^1$ is ($C_2$-$C_6$)alkenyl, is hydroborated to afford a compound of Formula I wherein is hydroxy($C_2$-$C_6$)alkyl, (8) a compound of Formula I, wherein $R^1$ is ($C_2$-$C_6$)alkenyl, can be reacted with osmium tetroxide and N-methylmorpholine-N-oxide to afford a compound of Formula I wherein Fe is vicinal dihydroxy($C_2$-$C_6$)alkyl, (9) a compound of Formula I, wherein $R^1$ is $H_2$C=CH($C_o$-$C_4$)alkyl-, can be reacted with ozone followed by $NaBH_4$ to give a compound of Formula I wherein $R^1$ is ω-hydroxy($C_1$-$C_6$)alkyl.

(10) a compound of Formula I wherein $R^1$ is amino($C_1$-$C_6$)alkyl can be reacted with an ($C_1$-$C_6$)alkyl isocyanate to give a compound of Formula I wherein $R^1$ is ($C_1$-$C_6$)alkylaminocarbonylamino($C_1$-$C_6$)alkyl.

(11) a compound of Formula I wherein $R^1$ is amino($C_1$-$C_6$)alkyl can be reacted with an ($C_1$-$C_6$)alkyl chloroformate to give a compound of Formula I wherein is ($C_1$-$C_6$)alkoxycarbonylamino($C_1$-$C_6$)alkyl.

(12) a compound of Formula I wherein $R^1$ is amino($C_1$-$C_6$)alkyl can be reacted with chlorosulfonyl isocyanate or sulfamide to give a compound of Formula I wherein $R^1$ is aminosulfonylamino($C_1$-$C_6$)alkyl.

(13) a compound of Formula I wherein $R^1$ is amino($C_1$-$C_6$)alkyl can be reacted with a ($C_1$-$C_6$)alkylsulfamoyl chloride to give a compound of Formula I wherein $R^1$ is ($C_1$-$C_6$)alkylaminosulfonylamino($C_1$-$C_6$)alkyl.

(14) a compound of Formula I wherein $R^1$ is hydroxy($C_1$-$C_6$)alkyl can be reacted with chlorosulfonyl isocyanate to give a compound of Formula I wherein $R^1$ is aminosulfonyloxy($C_1$-$C_6$)alkyl.

(15) a compound of Formula I wherein $R^1$ is hydroxy($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^1$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$)alkyl.

(16) a compound of Formula I wherein $R^1$ is hydroxy($C_1$-$C_6$)alkyl can be reacted with $POCl_3$ to give a compound of Formula I wherein R' is $(HO)_2P(=O)O(C_1$-$C_6$)alkyl.

(17) a compound of Formula I wherein $Cy^1$ is substituted with bromine or iodine, $A^2$ is a bond and $Cy^2$ is hydrogen can be reacted with a cyclic amine in the presence of a palladium catalyst to give a compound of Formula I wherein $A^2$ is a bond and $Cy^2$ is a cyclic amino moiety attached through its nitrogen atom.

(18) a compound of Formula I wherein Q is $NR^5$ and $R^5$ is H can be reacted with an ($C_1$-$C_6$)alkyl halide in the presence of a strong base such as sodium hydride to afford a compound of Formula I wherein Q is $NR^5$ and $R^5$ is ($C_1$-$C_6$)alkyl.

(19) a compound of Formula I wherein $R^1$ ω-$H_2$NCO($C_1$-$C_5$)alkyl can be reacted with TFAA in the presence of pyridine to afford a compound of Formula I wherein $R^1$ is ω-cyano($C_1$-$C_5$)alkyl.

(20) a compound of Formula I, wherein $R^1$ is ω-$MeO_2$C($C_1$-$C_5$)alkyl can be reacted with at least 2 equivalents of MeMgBr to afford a compound of Formula I, wherein $R^1$ or $HOC(Me)_2(C_1$-$C_5$)alkyl.

(21) a compound of Formula I wherein $R^1$ is ω-hydroxy ($C_1$-$C_6$)alkyl can be converted to its methanesulfonate or trifluoromethanesulfonate and reacted with morpholine to give a compound of Formula I, wherein $R^1$ is ω-(4-morpholino)($C_1$-$C_6$)alkyl.

The synthetic methods described above are generally applicable when R is

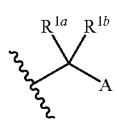

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 [LC-MS (3 min)]

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
| --- | --- | --- |
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 µm | |
| --- | --- | --- |
| Mobile Phase | A: water (4 L) + TFA (1.5 mL)) B: acetonitrile (4 L) + TFA (0.75 mL)) | |
| | TIME (min) | A % | B % |
| | 0 | 90 | 10 |
| | 2.2 | 20 | 80 |
| | 2.5 | 20 | 80 |
| Flow Rate | 1 mL/min | |
| Wavelength | UV 220 nm | |
| Oven Temp | 50° C. | |
| MS ionization | ESI | |

EXAMPLE 1

(S)-6-phenyl-3-m-tolyl-1,3-oxazinan-2-one

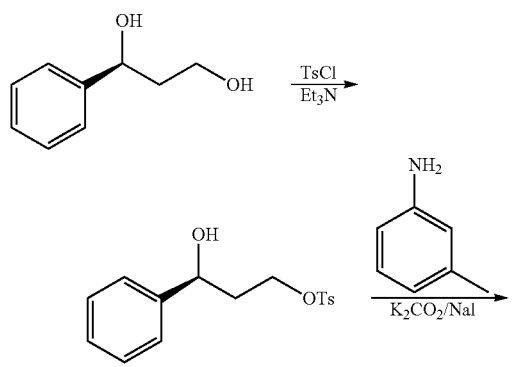

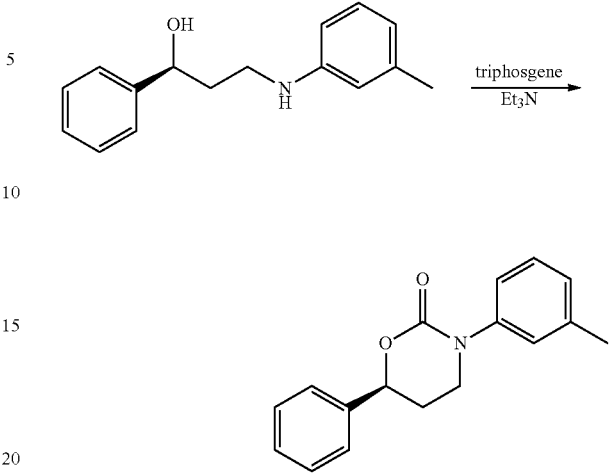

Step 1

To a solution of (S)-1-phenylpropane-1,3-diol (500 mg, 3.28 mmol) and triethylamine (399 mg, 3.94 mmol) in CH$_2$Cl$_2$ (5 mL) was added 4-methylbenzene-1-sulfonyl chloride (626 mg, 3.28 mol) slowly at 0° C., and the reaction mixture was stirred at rt for 2 h. The reaction solution was dried over Na$_2$SO$_4$ and concentrated to give the crude product, which was purified by preparative TLC (3:1 Petroleum ether/EtOAc) to give (S)-3-hydroxy-3-phenylpropyl 4-methylbenzenesulfonate (576 mg, 57%). $^1$H NMR (400 MHz, CDCl$_3$): δ=1.91-2.00 (m, 3H), 2.48 (s, 2H), 4.00 (m; 1H), 4.22 (m, 1H), 4.75 (m, 2H), 7.25-7.30 (m, 7H), 7.75 (d, 2H).

Step 2

To a solution of the (S)-3-hydroxy-3-phenylpropyl 4-methylbenzenesulfonate (100 mg, 0.33 mmol) in anhydrous acetonitrile (2 mL) were added K$_2$CO$_3$ (91 mg, 0.66 mmol), NaI (12 mg, 0.0825 mmol) and m-toluidine (42 mg, 0.39 mmol). The mixture was refluxed overnight. The mixture was filtered, and the filter cake was washed with EtOAc. The filtrate was concentrated to give the crude product, which was purified by preparative TLC (3:1 Petroleum ether/EtOAc) to give (S)-3-(m-tolylamino)-1-phenylpropan-1-ol (45 mg, 57%). $^1$H NMR (400 MHz, CDCl$_3$): δ=2.05 (m, 2H), 2.25 (s, 3H), 3.25 (m, 2H), 3.40 (s, 2H), 4.90 (m, 1H), 6.50 (m, 4H), 7.05 (m, 1H), 7.30 (m, 1H), 7.40 (d, 3H).

Step 3

To a solution of (S)-3-(m-tolylamino)-1-phenylpropan-1-ol (40 mg, 0.17 mmol) in dry CH$_2$Cl$_2$ (1 mL) was added triethylamine (50 mg, 0.51 mmol) and bis(trichloromethyl) carbonate (20 mg, 0.067 mmol) at 0° C., and the reaction mixture was stirred overnight at room temperature. When the reaction was over, the mixture was concentrated to give the crude product, which was purified by preparative TLC (3:1 Petroleum ether/EtOAc) to give (S)-6-phenyl-3-m-tolyl-1,3-oxazinan-2-one (12 mg, 26%). $^1$H NMR: (400 MHz, CDCl$_3$): δ=2.24-2.37 (m, 5H), 3.52-3.63 (m, 1H), 3.70-3.79 (m, 1H), 5.42 (dd, 1H), 7.01-7.10 (m, 3H), 7.18-7.23 (m, 2H), 7.32-7.39 (m, 4H).

EXAMPLE 2

(R)-6-phenyl-3-m-tolyl-1,3-oxazinan-2-one

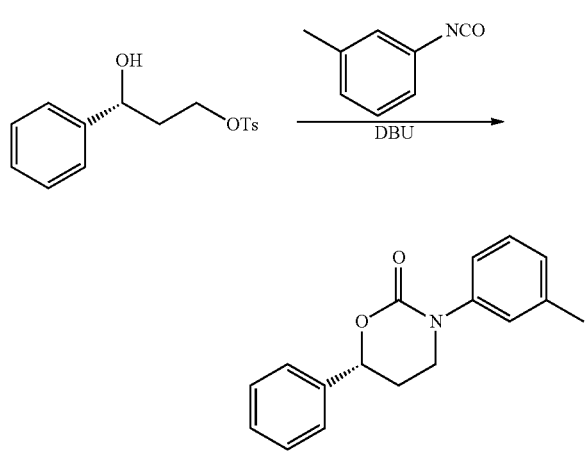

To a solution of (R)-3-hydroxy-3-phenylpropyl 4-methylbenzenesulfonate (100 mg, 0.327 mmol) and 1-isocyanato-3-methylbenzene (44 mg, 0.327 mmol) in $CH_2Cl_2$ (2 mL) was added DBU (149 mg, 0.981 mmol) and the reaction mixture was refluxed overnight. After the solvent was removed under reduced pressure, the residue was separated by preparative HPLC to give (R)-6-phenyl-3-m-tolyl-1,3-oxazinan-2-one (5.34 mg, 6%:). LC-MS (10-80) $t_R$=2.439 min, m/z=268; $^1$H NMR ($CDCl_3$): 2.30-2.34 (m, 5H), 3.63-3.68 (m, 1H), 3.80-3.86 (m, 1H), 5.49 (dd, 1H), 7.09-7.45 (m, 9H).

EXAMPLE 3

(R)-3-(naphthalen-1-yl)-6-phenyl-1,3-oxazinan-2-one

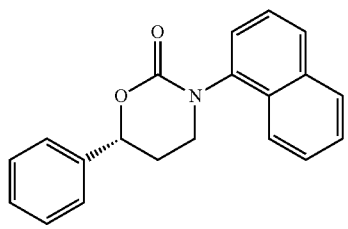 [SMILES: O=C1O[C@@H](c2ccccc2)CCN1c1cccc2ccccc12]

The title compound was prepared following a procedure analogous to that described in Example 2 using (R)-3-hydroxy-3-phenylpropyl 4-methylbenzenesulfonate and 1-isocyanatonaphthalene. LC-MS (10-80) $t_R$=2.625 min, m/z=304; $^1$H NMR ($CDCl_3$) δ 2.44-2.55 (m, 3H), 3.64-3.69 (m, 1H), 3.84-3.91 (m, 1H), 5.62-5.72 (m, 1 H), 7.38-7.61 (m, 9H), 7.86-7.93 (m, 3H).

EXAMPLE 4

3-(3-bromophenyl)-6-(2-chlorophenyl)-1,3-oxazinan-2-one

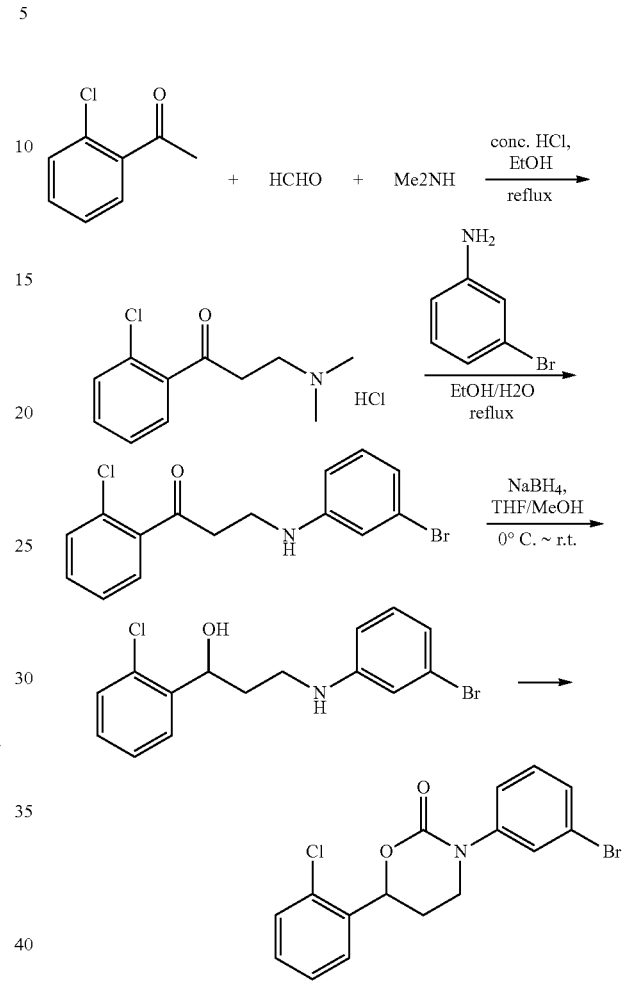

Step 1

At 0° C., concentrated HCl was added dropwise to $Me_2NH$ (40% in water, 5.57 mL, 1.1 equiv) to acidify the amine. After the addition, 1-(2-chlorophenyl)ethanone (6.18 g, 0.04 mol) and paraformaldehyde (1.68 g, 1.4 equiv) were added. The mixture was dissolved in ethanol (20 mL) and heated to reflux for 30 h. LC-MS found the starting material was gone. The reaction mixture was cooled to rt. The volatiles were removed in vacuo. EtOAc (30 mL) was added and the suspension was stirred for 15 min. The solid was collected by filtration and washed with EtOAc (2×5 mL). The white solid was dried under vacuum to afford 1-(2-chlorophenyl)-3-(dimethylamino)propan-1-one HCl salt (5.17 g, 61% yield). LC-MS (3 min) $t_R$=0.72 min, m/z 212, 214(M+1).

Step 2

A solution of 1-(2-chlorophenyl)-3-(dimethylamino)propan-1-one HCl salt (5.17 g, 20.85 mmol) and 3-bromoaniline (2.27 mL, 1 equiv) in 1:1 ethanol/water (21 mL, 1.0M) was heated at reflux overnight. LC-MS found the starting material was gone. The reaction mixture was cooled to rt. The ethanol was removed in vacuo. The residue was partitioned between EtOAc and water. The organic layer was washed with 1% aq HCl (2×30 mL), satd aq $NaHCO_3$ solution (20 mL), brine (20 mL), and dried over $Na_2SO_4$. After filtration and concentration, the residue (6.08 g) was purified by chromatography on a 120-g silica cartridge to afford 3-(3-bromophenylamino)-1-(2-chlorophenyl)propan-1-one (2.75 g, 40% yield) as an orange oil. LC-MS (3 min) $t_R$=2.03 min, m/z=340, 341(M+1); $^1$H NMR (CDCl$_3$) δ 7.47(d, 1H), 7.44-7.38 (m, 2H), 7.33 (td, 1H), 7.00 (m, 1H), 6.84 (m, 1H), 6.77 (s, 1H), 6.56 (m, 1H).

Step 3

A solution of 3-(3-bromophenylamino)-1-(2-chlorophenyl)propan-1-one (50 mg, 0.148 mmol) in 4:1 THF/methanol (5 mL) was cooled to 0° C. NaBH$_4$ (11 mg, 2 equiv) was added. After 10 min, the mixture was warmed up to rt slowly and stirred for 2 h. The mixture was concentrated, diluted with EtOAc (7 mL), washed with 1% aq HCl (1 mL), and dried over Na$_2$SO$_4$. Filtration and concentration afforded crude 3-(3-bromophenylamino)-1-(2-chlorophenyl)propan-1-ol which was used without further purification. LC-MS (3 min) $t_R$=1.93 min, m/z=342,343(M+1).

Step 4

Half of the crude 3-(3-bromophenylamino)-1-(2-chlorophenyl)propan-1-ol (0.074 mmol) was mixed with triphosgene (7.5 mg, 0.34 equiv), i-Pr$_2$NEt (26 μL, 2 equiv), pyridine (30 μL, 5 equiv) and acetonitrile (5 mL). The mixture was put in the microwave oven for 30 min at 110° C. LC-MS found the reaction completed. The mixture was concentrated, redissolved in EtOAc (5 mL), washed with 1% aq HCl (2×2 mL), concentrated and purified by preparative HPLC to afford 3-(3-bromo-phenyl)-6-(2-chloro-phenyl)-[1,3]oxazinan-2-one (15.2 mg). LC-MS (3 min) $t_R$=1.86 min., m/z 368,369 (M+1). $^1$H NMR (CDCl$_3$) δ 7.63(d, 1H), 7.56 (s, 1H), 7.43-7.26 (m, 6H), 5.83 (d, 1H), 3.88 (q, 1H), 3.67 (m, 1H), 2.55 (d, 1H), 2.17 (m, 1H).

EXAMPLE 5

1-((1S)-1-(2',4'-difluorobiphenyl-4-yl)ethyl)-4-phenylpiperidin-2-one

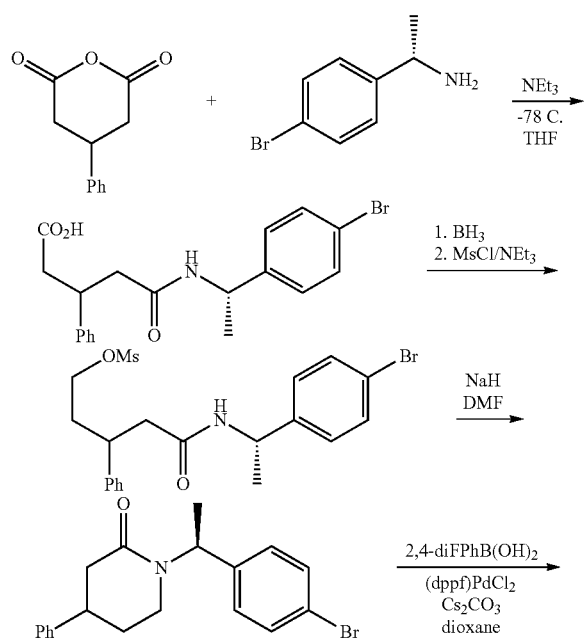

-continued

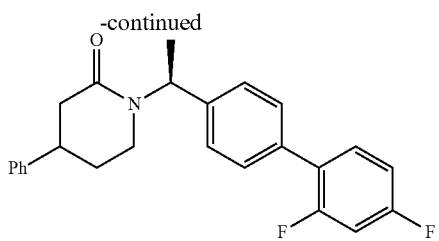

Step 1

3-Phenylglutaric anhydride (1.0 g, 5.26 mmol, 1.0 equiv) was dissolved in toluene (42 mL) and the solution cooled to −78° C. under an N$_2$ atmosphere. In a separate flask triethylamine (0.75 mL, 542 mg, 5.35 mmol, 1.05 equiv) and (R)-1-(4-bromophenyl)ethanamine (1163 mg, 5.79 mmol, 1.25 equiv) were dissolved in 21 mL of toluene and this solution added drop-wise via syringe over a 0.5 h period and the resulting solution was allowed to stir overnight while warming to rt. After this time 1.0 M aq HCl (~50 mL) was added and the mixture was transferred to a separatory funnel. The layers were separated and the organic layer washed with brine, dried over Na$_2$SO$_4$, filtered and evaporated. The resulting 5-((S)-1-(4-bromophenyl)ethylamino)-5-oxo-3-phenylpentanoic acid (1.92 g, 93%) was of sufficient purity to use in the next step.

Step 2

5-((S)-1-(4-bromophenyl)ethylamino)-5-oxo-3-phenylpentanoic acid (1.92 g, 4.92 mmol, 1.0 equiv) was dissolved in THF (30 mL) and the resulting solution cooled to 0° C. Borane (1.0 M in THF, 10.5 mL, 10.5 mmol, 2.1 equiv) was added via syringe. After 0.5 h LC-MS showed formation of the alcohol. The excess borane was quenched by the drop-wise addition of 1.0 M aq HCl and the mixture was transferred to a separatory funnel. The layers were separated and the organic layer washed with brine, dried over Na$_2$SO$_4$, filtered and evaporated. The resulting N—((S)-1-(4-bromophenyl)ethyl)-5-hydroxy-3-phenylpentanamide (~1.9 g, >95% yield) was of sufficient purity to use in the next step.

Step 3

N—((S)-1-(4-bromophenyl)ethyl)-5-hydroxy-3-phenylpentanamide (~1.9 g, 5 mmol, 1.0 equiv) was dissolved in CH$_2$Cl$_2$ (30 mL) and cooled to 0° C. Methanesulfonyl chloride (1.15 g, 10 mmol, 2.0 equiv) and triethylamine (2.1 g, 20 mmol, 4.0 equiv) were added sequentially and the resulting mixture stirred for 1 h. After this time LC-MS analysis showed consumption of the starting alcohol. The mixture was transferred to a separatory funnel and the organic layer was washed with 0.1 M aq HCl and brine, dried over Na$_2$SO$_4$, filtered and evaporated. The mesylate was purified by flash chromatography on silica, eluting with 0-47% EtOAc in hexanes. This provided 5-((S)-1-(4-bromophenyl)ethylamino)-5-oxo-3-phenylpentyl methanesulfonate (834 mg, 37%).

Step 4

Sodium hydride (60% in oil, 294 mg, 7.4 mmol, 4.0 equiv) was slurried in DMF (10 mL) and cooled to 0° C. 5-((S)-1-(4-bromophenyl)ethylamino)-5-oxo-3-phenylpentyl methanesulfonate (834 mg, 1.8 mmol, 1.0 equiv) was dissolved in DMF (5 mL) and the solution added via syringe to the NaH slurry. The flask was rinsed with DMF and the mixture was stirred for 2 h. After this time the mesylate was consumed. The DMF was removed and the residue was taken up in EtOAc/H$_2$O.

The layers were separated and the organic layer was washed with brine, dried over Na$_2$SO$_4$, filtered and evaporated. The lactam was purified by flash chromatography to provide 1-((S)-1-(4-bromophenyl)ethyl)-4-phenylpiperidin-2-one (291 mg, 81%).

Step 5

1-((S)-1-(4-bromophenyl)ethyl)-4-phenylpiperidin-2-one (291 mg, 0.813 mmol, 1.0 equiv), PdCl$_2$(dppf) (17 mg, 0.020 mmol, 2.5 mol %), Cs$_2$CO$_3$ (530 mg, 1.63 mmol. 2.0 equiv), and 2,4-difluorophenylboronic acid (194 mg, 1.72 mmol, 1.5 equiv) were added to a flask which was evacuated and backfilled with nitrogen, This was repeated twice. Dioxane (20 mL) was added and the red mixture heated to 70° C. under nitrogen for 17 h. After this time LC-MS showed formation of the biaryl. The mixture diluted with EtOAc/H$_2$O and transferred to a separatory funnel. The organic layer washed with brine, dried over Na$_2$SO$_4$, filtered and evaporated. The biaryl was purified by flash chromatography. A small portion was purified by prep HPLC to provide the above biaryl-lactam as a mixture of epimers. LC-MS (3 min): $t_R$=2.13 min, m/z=392.
$^1$H NMR (CD$_3$OD): δ 7.54-7.42 (m, 5H), 7.32-7.20 (m, 5H), 7.07-7.02 (m, 2H), 6.08 (q, J=7.0 Hz, 1H), 3.28 (m, 1H), 3.07 (m, 1H), 2.89 (m, 1H), 2.75 (m, 1H), 2.58 (m, 1H), 2.0 (m, 2H), 1.56 (d, J=7 Hz, 3H) ppm. The methyl group of the minor diastereomer, ~10%, is observed at 1.61 ppm with a similar coupling constant.
$^{19}$F NMR (CD$_3$OD): δ –113.8 ("sept"), –115,8 ("q").

EXAMPLE 6

4(-4-fluorophenyl)-1-((1S)-1-(4-methoxylphenyl)ethyl)piperidin-2-one

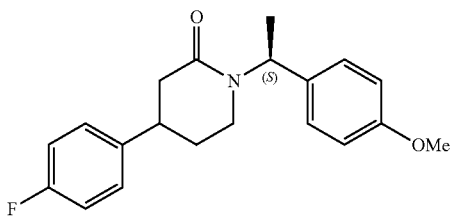

The title compound was prepared following procedures analogous to those described in Example 5 Step 1-4 using 3-(4-fluorophenylglutaric anhydride and (S)-1-(4-methoxyphenyl)ethanamine in Step 1. LC-MS (3 min): $t_R$=1.79 min, m/z=350. $^1$H NMR (CD$_3$OD): 7.25 (m, 4H), 7.01 (m, 2H), 6.90 (m, 2), 5.99 (bt, 1H), 3.76 (s, 3H), 3.1-2.2 (m, 2H), 2.74 (m, 1H), 2.54 (m, 2H), 1.98-1.82 (m, 2H), 1.53 and 1.48 (d, J=7 Hz, 3H). The two diastereomers are observed in ~2:1 ratio. $^{19}$F NMR (CD$_3$OD): δ –119.

EXAMPLE 7

3-((1S)-1-(4-bromophenyl)ethyl)-6-(4-fluorophenyl)-1,3-oxazinan-2-one

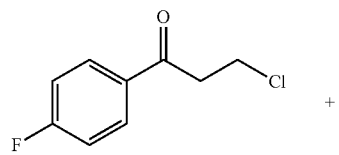

+

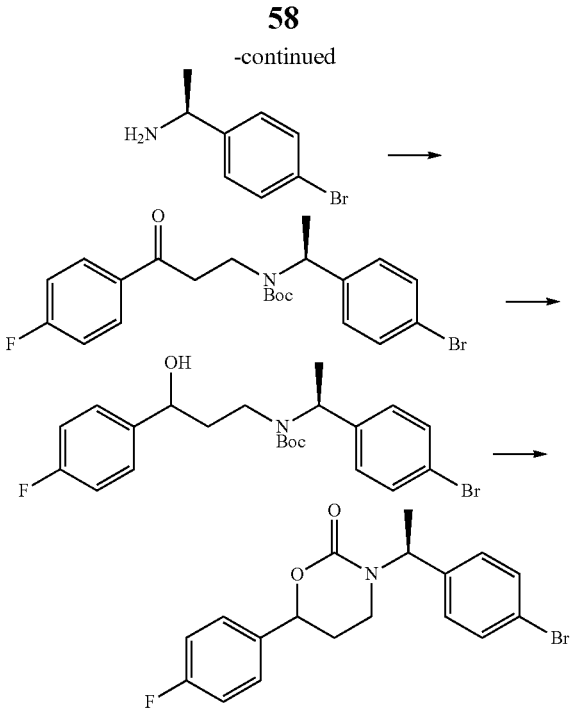

Step 1

To a stirred solution of 3-chloro-1-(4-fluorophenyl)propan-1-one (789 mg, 4.23 mmol) and i-Pr$_2$NEt (0.91 mL, 5.1 mmol) in THF (10 mL) was added (S)-1-(4-bromophenyl)ethanamine (0.68 mL, 4.65 mmol). The mixture was stirred overnight at rt and 10% aq K$_2$CO$_3$ (10 mL) and di-tert-butyl dicarbonate (1.38 g, 6.35 mmol) were added. The mixture was stirred overnight at rt and concentrated under reduced pressure. The aqueous residue was extracted with ether (100 mL). The ether extract was washed with 5% aq HCl (20 mL), satd aq NaHCO$_3$ (20 mL) and brine (20 mL), and dried over Na$_2$SO$_4$. Removal of the solvent left an oil (3.77 g) which was purified by chromatography on a 40-g silica gel cartridge eluted with a 0-60% EtOAc in hexanes gradient to afford (5)-tert-butyl 1-(4-bromophenyl)ethyl(3-(4-fluorophenyl)-3-oxopropyl)carbamate (2.04 g, quant) as a waxy solid. LC-MS (3 min) $t_R$=2.35 min, m/z=474, 472, 452, 450, 352, 350.

Step 2

To a stirred solution of (S)-tert-butyl 1-(4-bromophenyl)ethyl(3-(4-fluorophenyl)-3-oxopropyl)carbamate (500 mg, 1.11 mmol) in MeOH (20 mL) was added an NaBH$_4$ caplet (1 g, 26 mmol). The mixture was stirred at rt overnight and concentrated under reduced pressure. The residue was partitioned between EtOAc (80 mL) and water (20 mL). The organic layer was washed with brine, dried over Na$_2$SO$_4$ and concentrated to leave tert-butyl (S)-1-(4-bromophenyl)ethyl (3-(4-fluorophenyl)-3-hydroxypropyl)carbamate (474 mg, 94%) as an oil. LC-MS (3 min) $t_R$=2.33 min, 454. 452, 380, 378.

Step 3

To a stirred solution of tert-butyl (S)-1-(4-bromophenyl)ethyl(3-(4-fluorophenyl)-3-hydroxypropyl)carbamate (474 mg, 1.05 mmol) in dry THF (10 mL) was added 60% NaH in oil (250 mg, 10.4 mmol). The mixture was heated at reflux for 3 h. The mixture was diluted with water (20 mL) and. EtOAc (80 mL). The organic layer was separated, washed with 5% aq HCl (20 mL), satd aq NaHCO$_3$ (20 mL) and brine (20 mL), and dried over Na$_2$SO$_4$. Removal of the solvent left an oil (348 mg). A portion of the crude product was purified by preparative HPLC to afford 3-((1S)-1-(4-bromophenyl)

ethyl)-6-(4-fluorophenyl)-1,3-oxazinan-2-one as a 2:1 mixture of diastereomers based on $^1$H NMR. LC-MS (3 min) $t_R$=1.92 min, m/z=380, 378. $^1$H NMR (CDCl$_3$) δ [selected resonances of major and minor diastereomers] 1.52 (d, major), 1.59 (d, minor), 3.06 (m, major), 3.31 (m, minor), 5.20 (dd, major), 5.25 (dd, minor).

EXAMPLE 8

1-((S)-1-(4-bromophenyl)ethyl)-4-phenyl-1,3-diazepan-2-one

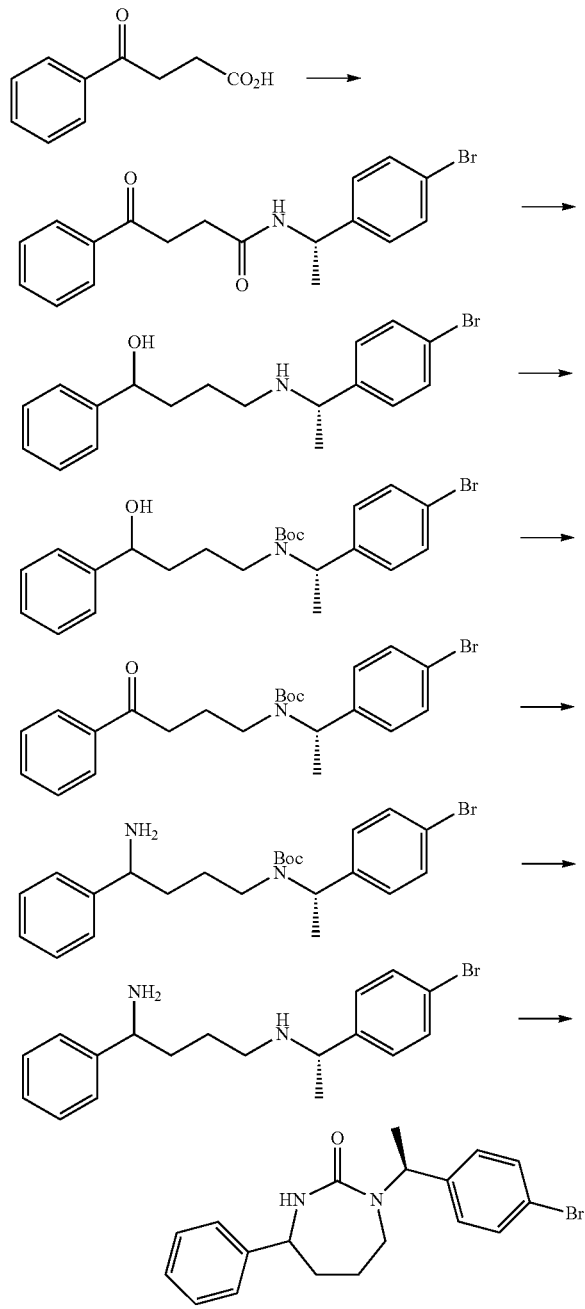

Step 1

To a stirred solution of benzoylpropionic acid (2.00 g, 11.2 mmol), (S)-1-(4-bromophenyl)ethanamine (2.25 g, 11.2 mmol), HOBt (1.72 g, 11.2 mmol) and i-Pr$_2$NEt (2.2 mL, 12.3 mmol) in CH$_2$Cl$_2$ (40 mL) was added EDC.HCl (2.37 g, 12.3 mmol). The mixture was stirred at rt for 4 h and diluted with EtOAc (140 mL) and 5% aq HCl (50 mL). The mixture was filtered and (S)—N-(1-(4-bromophenyl)ethyl)-4-oxo-4-phenylbutanamide (3.80 g, 93%) was collected as a white solid. $^1$H NMR (d$_6$-DMSO) δ 1.28 (d, 3H), 2.50 (m, 2H), 3.19 (m, 2H), 4.82 (m, 1H), 7.23 (d, 2H), 7.47 (4H), 7.59 (m, 1H), 7.92 (d, 2H), 8.38 (d, 1H).

Step 2

A 250-mL RBF equipped with a magnetic stirbar was charged with solid (S)—N-(1-(4-bromophenyl)ethyl)-4-oxo-4-phenylbutanamide (2.85 g, 7.9 mmol) and placed in an ice bath. To the stirred solid was added 1.0 M BH$_3$ in THF (30 mL, 30 mmol). The ice bath was removed and the mixture was stirred at rt for 2.5 h. The mixture was poured into 5% aq HCl (100 mL) and concentrated under reduced pressure to remove the THF. The aqueous residue was basified to pH 14 by portionwise addition of NaOH pellets. The mixture was extracted with CH$_2$Cl$_2$ (2×100 mL). The combined CH$_2$Cl$_2$ extracts were dried over Na$_2$SO$_4$. Removal of the solvent afforded crude 4-((S)-1-(4-bromophenyl)ethylamino)-1-phenylbutan-1-ol (2.58° g, 94%) as an oil. LC-MS Method 1 $t_R$=1.20 min, m/z=348, 350.

Step 3

To a stirred solution of crude 4-((S)-1-(4-bromophenyl)ethylamino)-1-phenylbutan-1-ol (2.46 g, 7.1 mmol) in THF (40 mL) was added 10% aq K$_2$CO$_3$ (40 mL), followed by di-t-butyl dicarbonate (1.90 g, 8.5 mmol). The mixture was stirred overnight at rt and concentrated to remove THF. The aqueous residue was extracted with EtOAc (2×80 mL). The combined EtOAc extracts were washed with brine (40 mL) and dried over MgSO$_4$. Removal of the solvent left tert-butyl (S)-1-(4-bromophenyl)ethyl(4-hydroxy-4-phenylbutyl)carbamate (3.24 g, quant). LC-MS Method 1 $t_R$=1.20 min, m/z=472, 470, 350, 348.

Step 4

To a stirred solution of tert-butyl (S)-1-(4-bromophenyl)ethyl(4-hydroxy-4-phenylbutyl)carbamate (3.24 g, 7.1 mmol) in CH$_2$Cl$_2$ (20 mL) at rt was added 15% Dess-Martin periodinane solution in CH$_2$Cl$_2$ (23 mL, 10.8 mmol). The mixture was stirred overnight at rt. Satd aq NaHCO$_3$ (50 mL) was added and the mixture was stirred for 10 min. Solid Na$_2$S$_2$O$_3$ (5 g) was added and stirring was continued for 1 h. The mixture was extracted with CH$_2$Cl$_2$ (2×100 mL) and the combined organic layer was washed with brine (35 mL) and dried over Na$_2$SO$_4$. Removal of the solvent left an amber oil (3.19 g) which was purified by chromatography on a 40-g silica cartridge eluted with a 0-100% EtOAc in hexanes gradient to afford (S)-tert-butyl 1-(4-bromophenyl)ethyl(4-oxo-4-phenylbutyl)carbamate (2.32 g, 72%) as a yellow oil. LC-MS Method 1 $t_R$=2.40 min, m/z=470, 468, 348, 346.

Step 5

To a stirred solution of (S)-tert-butyl 1-(4-bromophenyl)ethyl(4-oxo-4-phenylbutyl)carbamate (193 mg, 0.43 mmol) and NH$_4$OAc (670 mg, 8.6 mmol) in MeOH (15 mL) was added NaCNBH$_3$ (270 mg, 4.3 mmol). The mixture was heated at reflux for 22 h and concentrated under reduced pressure. The residue was partitioned between 1 M aq NaOH (25 mL) and CH$_2$Cl$_2$ (2×50 mL). The combined CH$_2$Cl$_2$ layers were washed with brine (15 mL), dried over Na$_2$SO$_4$ and concentrated to afford tert-butyl 4-amino-4-phenylbutyl ((1S)-1-(4-bromophenyl)ethyl)carbamate (179 mg, 93%) as an oil which was used without further purification. LC-MS Method 1 $t_R$=1.57 min, m/z=449, 447.

Step 6

To a stirred solution of tert-butyl 4-amino-4-phenylbutyl ((1S)-1-(4-bromophenyl)ethyl)carbamate (179 mg, 0.40 mmol) in $CH_2Cl_2$ (5 mL) at rt was added 4 M HCl in dioxane (5 mL). The mixture was stirred for 1 h and concentrated to afford $N^1$-((1S)-1-(4-bromophenyl)ethyl)-4-phenylbutane-1,4-diamine dihydrochloride (162 mg, 96%). LC-MS Method 1 $t_R$=0.92 min, m/z=349, 347.

Step 7

A stirred solution of $N^1$—((1S)-1-(4-bromophenyl)ethyl)-4-phenylbutane-1,4-diamine dihydrochloride (19.5 mg, 0.046 mmol) and i-$Pr_2$NEt (0.10 mL, 0.56 mmol) in $CH_2Cl_2$ (8 mL) was cooled in an ice bath and solid triphosgene (4.6 mg, 0.015 mmol) was added. The ice bath was allowed to melt and the mixture was stirred overnight at rt. The mixture was diluted with ether (90 mL), washed with 5% aq HCl (20 mL) and satd aq $NaHCO_3$ (20 mL), and dried over $MgSO_4$. Removal of the solvent left a residue (17.5 mg) which was purified by preparative HPLC to afford 1-((S)-1-(4-bromophenyl)ethyl)-4-phenyl-1,3-diazepan-2-one (1.4 mg, 8%). LC-MS (3 min) $t_R$=2.05 min, m/z=375, 373.

BIOLOGICAL TEST EXAMPLE 1

The inhibition of microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxysteroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM $MgCl_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2, Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE

| | OF BIOLOGICAL ASSAY RESULTS | | |
|---|---|---|---|
| | | Biological Test Example 1 | |
| Compound | $IC_{50}$ Range[a] | Average % inhibition at 100 nM | Average % inhibition at 111.1 nM |
| EXAMPLE 1 | + | 13.7 | |
| EXAMPLE 2 | + | | 27.2 |
| EXAMPLE 3 | + | | −5.9 |
| EXAMPLE 4 | + | | 22.5 |
| EXAMPLE 5 | ++ | 94.5 | |
| EXAMPLE 6 | ++ | 89.4 | |
| EXAMPLE 7 | ++ | 90.1 | |
| EXAMPLE 8 | ++ | 100.3 | |

[a]++ means $IC_{50}$ = <100 nM, + means $IC_{50}$ = 100-1000 nM, # means $IC_{50}$ > 100 nM, − means $IC_{50}$ > 1000 nM.

TABLE-continued

PROPHETIC COMPOUNDS

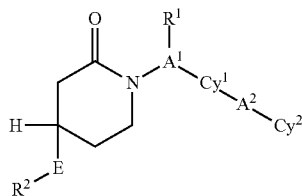

| Compound No | A¹—R¹ | Cy¹ | A2 | Cy² | E | R² |
|---|---|---|---|---|---|---|
| 1a | CHMe | Ph | bond | H | bond | Ph |
| 2a | CHMe | 4-Cl—Ph | bond | H | bond | i-Pr |
| 3a | CHMe | Ph | bond | H | bond | 2-Me—Ph |
| 4a | CHMe | Ph | bond | H | bond | 4-Me—Ph |
| 5a | CHMe | Ph | bond | H | bond | 4-F—Ph |
| 6a | CHMe | c-hex | bond | H | bond | 4-F—Ph |
| 7a | CHMe | 3-MeO—Ph | bond | H | bond | Ph |
| 8a | CHMe | 4-HOCH₂—Ph | bond | H | bond | Ph |
| 9a | CHMe | 4-MeO—Ph | bond | H | bond | Ph |
| 10a | CHMe | 4-Me—Ph | bond | H | bond | 4-F—Ph |
| 11a | CHMe | 4-Cl—Ph | bond | H | bond | Ph |
| 12a | CHMe | 3-F—Ph | bond | H | bond | 4-F—Ph |
| 13a | CHMe | 2-F—Ph | bond | H | bond | 4-F—Ph |
| 14a | CHMe | 4-F—Ph | bond | H | bond | 4-F—Ph |
| 15a | CHMe | 4-HOCH₂CH₂—Ph | bond | H | bond | Ph |
| 16a | CHMe | 4-MeOCH₂—Ph | bond | H | bond | Ph |
| 17a | CHMe | 4-Br—Ph | bond | H | bond | i-Pr |
| 18a | CHMe | Ph | bond | H | bond | 4-MeS—Ph |
| 19a | CHMe | 4-HOCH₂—Ph | bond | H | bond | 4-F—Ph |
| 20a | CHMe | 4-MeO—Ph | bond | H | bond | 4-F—Ph |
| 21a | bond | 1,3-C₆H₄ | bond | Ph | bond | Ph |
| 22a | bond | 3-Br—Ph | bond | H | bond | Ph |
| 23a | CHMe | 4-Cl—Ph | bond | H | bond | 4-F—Ph |
| 24a | CHMe | 1,4-C₆H₄ | bond | c-Pr | bond | 4-F—Ph |
| 25a | bond | 1-(t-BuOC═O)pyrrolidin-3-yl | bond | H | bond | Ph |
| 26a | bond | 1,3-C₆H₄ | bond | 3-F—Ph | bond | Ph |
| 27a | bond | 1,3-C₆H₄ | bond | 4-F—Ph | bond | Ph |
| 28a | bond | 1,3-C₆H₄ | bond | 2-F—Ph | bond | Ph |
| 29a | CHMe | Ph | bond | 3-pyrazolyl | bond | Ph |
| 30a | bond | 2,6-pyridyl | bond | 4-F—Ph | bond | Ph |
| 31a | CHMe | 4-(HOC(Me)₂CH₂—Ph | bond | H | bond | Ph |
| 32a | bond | 1,3-C₆H₄ | bond | 2-NC—Ph | bond | Ph |
| 33a | CHMe | 4-MeO₂C—Ph | bond | H | bond | 4-F—Ph |
| 34a | CHMe | 4-HOC(Me)₂—Ph | bond | H | bond | 4-F—Ph |
| 35a | CHMe | 1,4-C₆H₄ | bond | 4-pyridyl | bond | Ph |
| 36a | CHMe | 1,4-C₆H₄ | bond | 3-pyridyl | bond | Ph |
| 37a | CHMe | 1,4-C₆H₄ | bond | 2,4-diF—Ph | bond | i-Pr |
| 38a | bond | 1,3-C₆H₄ | bond | 2-MeO—Ph | bond | Ph |
| 39a | CHMe | 4-Br—Ph | bond | H | bond | Ph |
| 40a | CHMe | 1,4-C₆H₄ | bond | 2-thienyl | bond | Ph |
| 41a | bond | 1,3-C₆H₄ | bond | 2-Cl—Ph | bond | Ph |
| 42a | bond | 1,3-C₆H₄ | bond | 3-Cl—Ph | bond | Ph |
| 43a | bond | 1,3-C₆H₄ | bond | Ph | bond | 3-Cl—Ph |
| 44a | CHMe | 4-F2HCO—Ph | bond | H | bond | 4-F—Ph |
| 45a | bond | 1,3-C₆H₄ | bond | 2,5-diF—Ph | bond | Ph |
| 46a | bond | 1,3-C₆H₄ | bond | 3,5-diF—Ph | bond | Ph |
| 47a | bond | 1,3-C₆H₄ | bond | 2,4-diF—Ph | bond | Ph |
| 48a | bond | 1,3-C₆H₄ | bond | 4-F—Ph | bond | Ph |
| 49a | CHMe | 4-Br—Ph | bond | H | bond | 2-thienyl |
| 50a | bond | 1,3-C6H4 | bond | 2,4-diF—Ph | bond | 2-pyridyl |
| 51a | bond | 2,6-pyridyl | bond | 4-F—Ph | bond | 4-F—Ph |
| 52a | bond | 2,6-pyridyl | bond | 4-F—Ph | bond | 2-F—Ph |
| 53a | bond | 2,6-pyridyl | bond | 2,4-diF—Ph | bond | Ph |
| 54a | CHMe | 3-CF3—Ph | bond | H | bond | 4-F—Ph |
| 55a | CHMe | 4-CF3—Ph | bond | H | bond | 4-F—Ph |
| 56a | CHEt | 4-Br—Ph | bond | H | bond | Ph |
| 57a | CHMe | 1,4-C₆H₄ | bond | 2-oxo-5-(1,2-dihydropyridyl) | bond | Ph |
| 58a | CHMe | 1,4-C₆H₄ | bond | 1-oxo-3-pyridyl | bond | Ph |
| 59a | CHMe | 1,4-C₆H₄ | bond | 4-F—Ph | bond | Ph |
| 60a | CHMe | 1,4-C₆H₄ | bond | 3-pyridyl | bond | 4-F—Ph |
| 61a | CHMe | 1,4-C₆H₄ | bond | 5-F-3-pyridyl | bond | Ph |
| 62a | CHMe | 4-Br—Ph | bond | H | bond | 4-F—Ph |
| 63a | CHMe | 1,4-C₆H₄ | bond | 4-F—Ph | bond | 2-thienyl |

TABLE-continued

| | | | | | | |
|---|---|---|---|---|---|---|
| 64a | bond | 1,3-C$_6$H$_4$ | bond | 2-Cl-4-F—Ph | bond | Ph |
| 65a | bond | 2,6-pyridyl | bond | 2-Cl-4-F—Ph | bond | Ph |
| 66a | bond | 1,3-(4-F)C6H3 | bond | 4-F—Ph | bond | 4-F—Ph |
| 67a | bond | 1,3-(4-F)C6H3 | bond | 4-F—Ph | bond | 2-F—Ph |
| 68a | bond | 2,6-pyridyl | bond | 2,4-diF—Ph | bond | 4-F—Ph |
| 69a | bond | 2,6-pyridyl | bond | 2,4-diF—Ph | bond | 2-F—Ph |
| 70a | CHMe | 1,4-C$_6$H$_4$ | bond | 4-morpholinyl | bond | 4-F—Ph |
| 71a | CHMe | 1,4-C$_6$H$_4$ | bond | 2-MeO-5-pyridyl | bond | Ph |
| 72a | CHMe | 1,4-C$_6$H$_4$ | bond | 1-Me-6-oxo-3-(1,6-dihydropyridyl) | bond | Ph |
| 73a | CHEt | 1,4-C$_6$H$_4$ | bond | 4-F—Ph | bond | Ph |
| 74a | CHMe | 1,4-C$_6$H$_4$ | bond | 2-Me-4-pyridyl | bond | 4-F—Ph |
| 75a | CHEt | 4-Br—Ph | bond | H | bond | 4-F—Ph |
| 76a | CHMe | 1,4-C$_6$H$_4$ | bond | 4-F—Ph | bond | 4-F—Ph |
| 77a | CHMe | 1,4-C$_6$H$_4$ | bond | 2,4-diF—Ph | bond | Ph |
| 78a | CHMe | 1,4-C$_6$H$_4$ | bond | 4-F—Ph | bond | 3-F—Ph |
| 79a | CHMe | 1,4-C$_6$H$_4$ | bond | 4-F—Ph | bond | 2-F—Ph |
| 80a | CHMe | 1,4-C$_6$H$_4$ | bond | 5-F-3-pyridyl | bond | 4-F—Ph |
| 81a | CHMe | 1,4-C$_6$H$_4$ | bond | 5-Me-1,3,4-thiadiazol-2-yl | bond | 4-F—Ph |
| 82a | bond | 1,3-C$_6$H$_4$ | bond | 2,6-diCl—Ph | bond | Ph |
| 83a | CHMe | 1,4-C$_6$H$_4$ | bond | 2,4-diF—Ph | bond | 2-thienyl |
| 84a | bond | 2,6-pyridyl | bond | 2-Cl-4-F—Ph | bond | 4-F—Ph |
| 85a | bond | 2,6-pyridyl | bond | 2-Cl-4-F—Ph | bond | 2-F—Ph |
| 86a | bond | 2,6-(5-Cl)-pyridyl | bond | 4-F—Ph | bond | 2-F—Ph |
| 87a | bond | 1,3-(4-F)C$_6$H$_3$ | bond | 2,4-diF—Ph | bond | 4-F—Ph |
| 88a | bond | 1,3-(4-F)C$_6$H$_3$ | bond | 2,4-diF—Ph | bond | 2-F—Ph |
| 89a | CHMe | 1,4-C$_6$H$_4$ | bond | 5-MeCO-2-thienyl | bond | Ph |
| 90a | CHMe | 1,4-C$_6$H$_4$ | bond | 5-MeO-3-pyridyl | bond | 4-F—Ph |
| 91a | CHMe | 1,4-C$_6$H$_4$ | bond | 5-(H$_2$NCHMe)-2-thienyl | bond | Ph |
| 92a | CHEt | 1,4-C$_6$H$_4$ | bond | 2,4-diF—Ph | bond | Ph |
| 93a | CHEt | 1,4-C$_6$H$_4$ | bond | 4-F—Ph | bond | 4-F—Ph |
| 94a | CHMe | 1,4-C$_6$H$_4$ | bond | 5-(HOCHMe)-2-thienyl | bond | Ph |
| 95a | CHMe | 1,4-C$_6$H$_4$ | bond | 2,4-diMe-5-thiazolyl | bond | 4-F—Ph |
| 96a | CHMe | 1,4-C$_6$H$_4$ | bond | 5-Cl-3-pyridyl | bond | 4-F—Ph |
| 97a | CHMe | 1,4-C$_6$H$_4$ | bond | 2,4-diF—Ph | bond | 4-F—Ph |
| 98a | bond | 1,3-(4-F)C$_6$H$_3$ | bond | 2-Cl-4-F—Ph | bond | 4-F—Ph |
| 99a | bond | 2,6-(5-F)-pyridyl | bond | 2,4-diF—Ph | bond | 2-F—Ph |
| 100a | CHEt | 1,4-C$_6$H$_4$ | bond | 2,4-diF—Ph | bond | 4-F—Ph |
| 101a | CHMe | 1,4-C$_6$H$_4$ | bond | 3-(CF$_3$)-1-pyrazolyl | bond | 4-F—Ph |
| 102a | CHMe | 1,4-C$_6$H$_4$ | bond | 6-CF$_3$-3-pyridyl | bond | 4-F—Ph |

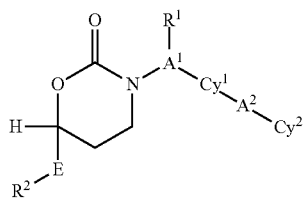

| | | | | | | |
|---|---|---|---|---|---|---|
| 1b | CHMe | Ph | bond | H | bond | Ph |
| 2b | CHMe | 4-Cl—Ph | bond | H | bond | i-Pr |
| 3b | CHMe | Ph | bond | H | bond | 2-Me—Ph |
| 4b | CHMe | Ph | bond | H | bond | 4-Me—Ph |
| 5b | CHMe | Ph | bond | H | bond | 4-F—Ph |
| 6b | CHMe | c-hex | bond | H | bond | 4-F—Ph |
| 7b | CHMe | 3-MeO—Ph | bond | H | bond | Ph |
| 8b | CHMe | 4-HOCH$_2$—Ph | bond | H | bond | Ph |
| 9b | CHMe | 4-MeO—Ph | bond | H | bond | Ph |
| 10b | CHMe | 4-Me—Ph | bond | H | bond | 4-F—Ph |
| 11b | CHMe | 4-Cl—Ph | bond | H | bond | Ph |
| 12b | CHMe | 3-F—Ph | bond | H | bond | 4-F—Ph |
| 13b | CHMe | 2-F—Ph | bond | H | bond | 4-F—Ph |
| 14b | CHMe | 4-F—Ph | bond | H | bond | 4-F—Ph |
| 15b | CHMe | 4-HOCH$_2$CH$_2$—Ph | bond | H | bond | Ph |
| 16b | CHMe | 4-MeOCH$_2$—Ph | bond | H | bond | Ph |
| 17b | CHMe | 4-Br—Ph | bond | H | bond | i-Pr |
| 18b | CHMe | Ph | bond | H | bond | 4-MeS—Ph |
| 19b | CHMe | 4-HOCH$_2$—Ph | bond | H | bond | 4-F—Ph |
| 20b | CHMe | 4-MeO—Ph | bond | H | bond | 4-F—Ph |
| 21b | bond | 1,3-C$_6$H$_4$ | bond | Ph | bond | Ph |
| 22b | bond | 3-Br—Ph | bond | H | bond | Ph |
| 23b | CHMe | 4-Cl—Ph | bond | H | bond | 4-F—Ph |
| 24b | CHMe | 1,4-C$_6$H$_4$ | bond | c-Pr | bond | 4-F—Ph |
| 25b | bond | 1-(t-BuOC=O)pyrrolidin-3-yl | bond | H | bond | Ph |
| 26b | bond | 1,3-C$_6$H$_4$ | bond | 3-F—Ph | bond | Ph |
| 27b | bond | 1,3-C$_6$H$_4$ | bond | 4-F—Ph | bond | Ph |

| | | | | | | | |
|---|---|---|---|---|---|---|---|
| 28b | bond | 1,3-C$_6$H$_4$ | bond | 2-F—Ph | bond | Ph | |
| 29b | CHMe | Ph | bond | 3-pyrazolyl | bond | Ph | |
| 30b | bond | 2,6-pyridyl | bond | 4-F—Ph | bond | Ph | |
| 31b | CHMe | 4-(HOC(Me)$_2$CH$_2$)—Ph | bond | H | bond | Ph | |
| 32b | bond | 1,3-C$_6$H$_4$ | bond | 2-NC—Ph | bond | Ph | |
| 33b | CHMe | 4-MeO$_2$C—Ph | bond | H | bond | 4-F—Ph | |
| 34b | CHMe | 4-HOC(Me)$_2$—Ph | bond | H | bond | 4-F—Ph | |
| 35b | CHMe | 1,4-C$_6$H$_4$ | bond | 4-pyridyl | bond | Ph | |
| 36b | CHMe | 1,4-C$_6$H$_4$ | bond | 3-pyridyl | bond | Ph | |
| 37b | CHMe | 1,4-C$_6$H$_4$ | bond | 2,4-diF—Ph | bond | i-Pr | |
| 38b | bond | 1,3-C$_6$H$_4$ | bond | 2-MeO—Ph | bond | Ph | |
| 39b | CHMe | 4-Br—Ph | bond | H | bond | Ph | |
| 40b | CHMe | 1,4-C$_6$H$_4$ | bond | 2-thienyl | bond | Ph | |
| 41b | bond | 1,3-C$_6$H$_4$ | bond | 2-Cl—Ph | bond | Ph | |
| 42b | bond | 1,3-C$_6$H$_4$ | bond | 3-Cl—Ph | bond | Ph | |
| 43b | bond | 1,3-C$_6$H$_4$ | bond | Ph | bond | 3-Cl—Ph | |
| 44b | CHMe | 4-F2HCO—Ph | bond | H | bond | 4-F—Ph | |
| 45b | bond | 1,3-C$_6$H$_4$ | bond | 2,5-diF—Ph | bond | Ph | |
| 46b | bond | 1,3-C$_6$H$_4$ | bond | 3,5-diF—Ph | bond | Ph | |
| 47b | bond | 1,3-C$_6$H$_4$ | bond | 2,4-diF—Ph | bond | Ph | |
| 48b | bond | 1,3-C$_6$H$_4$ | bond | 4-F—Ph | bond | Ph | |
| 49b | CHMe | 4-Br—Ph | bond | H | bond | 2-thienyl | |
| 50b | bond | 1,3-C6H4 | bond | 2,4-diF—Ph | bond | 2-pyridyl | |
| 51b | bond | 2,6-pyridyl | bond | 4-F—Ph | bond | 4-F—Ph | |
| 52b | bond | 2,6-pyridyl | bond | 4-F—Ph | bond | 2-F—Ph | |
| 53b | bond | 2,6-pyridyl | bond | 2,4-diF—Ph | bond | Ph | |
| 54b | CHMe | 3-CF3—Ph | bond | H | bond | 4-F—Ph | |
| 55b | CHMe | 4-CF3—Ph | bond | H | bond | 4-F—Ph | |
| 56b | CHEt | 4-Br—Ph | bond | H | bond | Ph | |
| 57b | CHMe | 1,4-C$_6$H$_4$ | bond | 2-oxo-5-(1,2-dihydropyridyl) | bond | Ph | |
| 58b | CHMe | 1,4-C$_6$H$_4$ | bond | 1-oxo-3-pyridyl | bond | Ph | |
| 59b | CHMe | 1,4-C$_6$H$_4$ | bond | 4-F—Ph | bond | Ph | |
| 60b | CHMe | 1,4-C$_6$H$_4$ | bond | 3-pyridyl | bond | 4-F—Ph | |
| 61b | CHMe | 1,4-C$_6$H$_4$ | bond | 5-F-3-pyridyl | bond | Ph | |
| 62b | CHMe | 4-Br—Ph | bond | H | bond | 4-F—Ph | |
| 63b | CHMe | 1,4-C$_6$H$_4$ | bond | 4-F—Ph | bond | 2-thienyl | |
| 64b | bond | 1,3-C$_6$H$_4$ | bond | 2-Cl-4-F—Ph | bond | Ph | |
| 65b | bond | 2,6-pyridyl | bond | 2-Cl-4-F—Ph | bond | Ph | |
| 66b | bond | 1,3-(4-F)C6H3 | bond | 4-F—Ph | bond | 4-F—Ph | |
| 67b | bond | 1,3-(4-F)C6H3 | bond | 4-F—Ph | bond | 2-F—Ph | |
| 68b | bond | 2,6-pyridyl | bond | 2,4-diF—Ph | bond | 4-F—Ph | |
| 69b | bond | 2,6-pyridyl | bond | 2,4-diF—Ph | bond | 2-F—Ph | |
| 70b | CHMe | 1,4-C$_6$H$_4$ | bond | 4-morpholinyl | bond | 4-F—Ph | |
| 71b | CHMe | 1,4-C$_6$H$_4$ | bond | 2-MeO-5-pyridyl | bond | Ph | |
| 72b | CHMe | 1,4-C$_6$H$_4$ | bond | 1-Me-6-oxo-3-(1,6-dihydropyridyl) | bond | Ph | |
| 73b | CHEt | 1,4-C$_6$H$_4$ | bond | 4-F—Ph | bond | Ph | |
| 74b | CHMe | 1,4-C$_6$H$_4$ | bond | 2-Me-4-pyridyl | bond | 4-F—Ph | |
| 75b | CHEt | 4-Br—Ph | bond | H | bond | 4-F—Ph | |
| 76b | CHMe | 1,4-C$_6$H$_4$ | bond | 4-F—Ph | bond | 4-F—Ph | |
| 77b | CHMe | 1,4-C$_6$H$_4$ | bond | 2,4-diF—Ph | bond | Ph | |
| 78b | CHMe | 1,4-C$_6$H$_4$ | bond | 4-F—Ph | bond | 3-F—Ph | |
| 79b | CHMe | 1,4-C$_6$H$_4$ | bond | 4-F—Ph | bond | 2-F—Ph | |
| 80b | CHMe | 1,4-C$_6$H$_4$ | bond | 5-F-3-pyridyl | bond | 4-F—Ph | |
| 81b | CHMe | 1,4-C$_6$H$_4$ | bond | 5-Me-1,3,4-thiadiazol-2-yl | bond | 4-F—Ph | |
| 82b | bond | 1,3-C$_6$H$_4$ | bond | 2,6-diCl—Ph | bond | Ph | |
| 83b | CHMe | 1,4-C$_6$H$_4$ | bond | 2,4-diF—Ph | bond | 2-thienyl | |
| 84b | bond | 2,6-pyridyl | bond | 2-Cl-4-F—Ph | bond | 4-F—Ph | |
| 85b | bond | 2,6-pyridyl | bond | 2-Cl-4-F—Ph | bond | 2-F—Ph | |
| 86b | bond | 2,6-(5-Cl)-pyridyl | bond | 4-F—Ph | bond | 2-F—Ph | |
| 87b | bond | 1,3-(4-F)C$_6$H$_3$ | bond | 2,4-diF—Ph | bond | 4-F—Ph | |
| 88b | bond | 1,3-(4-F)C$_6$H$_3$ | bond | 2,4-diF—Ph | bond | 2-F—Ph | |
| 89b | CHMe | 1,4-C$_6$H$_4$ | bond | 5-MeCO-2-thienyl | bond | Ph | |
| 90b | CHMe | 1,4-C$_6$H$_4$ | bond | 5-MeO-3-pyridyl | bond | 4-F—Ph | |
| 91b | CHMe | 1,4-C$_6$H$_4$ | bond | 5-(H$_2$NCHMe)-2-thienyl | bond | Ph | |
| 92b | CHEt | 1,4-C$_6$H$_4$ | bond | 2,4-diF—Ph | bond | Ph | |
| 93b | CHEt | 1,4-C$_6$H$_4$ | bond | 4-F—Ph | bond | 4-F—Ph | |
| 94b | CHMe | 1,4-C$_6$H$_4$ | bond | 5-(HOCHMe)-2-thienyl | bond | Ph | |
| 95b | CHMe | 1,4-C$_6$H$_4$ | bond | 2,4-diMe-5-thiazolyl | bond | 4-F—Ph | |
| 96b | CHMe | 1,4-C$_6$H$_4$ | bond | 5-Cl-3-pyridyl | bond | 4-F—Ph | |
| 97b | CHMe | 1,4-C$_6$H$_4$ | bond | 2,4-diF—Ph | bond | 4-F—Ph | |
| 98b | bond | 1,3-(4-F)C$_6$H$_3$ | bond | 2-Cl-4-F—Ph | bond | 4-F—Ph | |
| 99b | bond | 2,6-(5-F)-pyridyl | bond | 2,4-diF—Ph | bond | 2-F—Ph | |
| 100b | CHEt | 1,4-C$_6$H$_4$ | bond | 2,4-diF—Ph | bond | 4-F—Ph | |

| No. | E | R² | A¹ | Cy¹ | A² | Cy² |
|---|---|---|---|---|---|---|
| 101b | CHMe | 1,4-C₆H₄ | bond | 3-(CF₃)-1-pyrazolyl | bond | 4-F—Ph |
| 102b | CHMe | 1,4-C₆H₄ | bond | 6-CF₃-3-pyridyl | bond | 4-F—Ph |

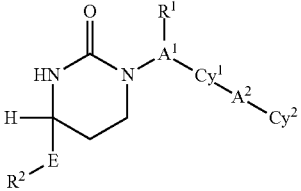

| No. | E | R² | A¹ | Cy¹ | A² | Cy² |
|---|---|---|---|---|---|---|
| 1c | CHMe | Ph | bond | H | bond | Ph |
| 2c | CHMe | 4-Cl—Ph | bond | H | bond | i-Pr |
| 3c | CHMe | Ph | bond | H | bond | 2-Me—Ph |
| 4c | CHMe | Ph | bond | H | bond | 4-Me—Ph |
| 5c | CHMe | Ph | bond | H | bond | 4-F—Ph |
| 6c | CHMe | c-hex | bond | H | bond | 4-F—Ph |
| 7c | CHMe | 3-MeO—Ph | bond | H | bond | Ph |
| 8c | CHMe | 4-HOCH₂—Ph | bond | H | bond | Ph |
| 9c | CHMe | 4-MeO—Ph | bond | H | bond | Ph |
| 10c | CHMe | 4-Me—Ph | bond | H | bond | 4-F—Ph |
| 11c | CHMe | 4-Cl—Ph | bond | H | bond | Ph |
| 12c | CHMe | 3-F—Ph | bond | H | bond | 4-F—Ph |
| 13c | CHMe | 2-F—Ph | bond | H | bond | 4-F—Ph |
| 14c | CHMe | 4-F—Ph | bond | H | bond | 4-F—Ph |
| 15c | CHMe | 4-HOCH₂CH₂—Ph | bond | H | bond | Ph |
| 16c | CHMe | 4-MeOCH₂—Ph | bond | H | bond | Ph |
| 17c | CHMe | 4-Br—Ph | bond | H | bond | i-Pr |
| 18c | CHMe | Ph | bond | H | bond | 4-MeS—Ph |
| 19c | CHMe | 4-HOCH₂—Ph | bond | H | bond | 4-F—Ph |
| 20c | CHMe | 4-MeO—Ph | bond | H | bond | 4-F—Ph |
| 21c | bond | 1,3-C₆H₄ | bond | Ph | bond | Ph |
| 22c | bond | 3-Br—Ph | bond | H | bond | Ph |
| 23c | CHMe | 4-Cl—Ph | bond | H | bond | 4-F—Ph |
| 24c | CHMe | 1,4-C₆H₄ | bond | c-Pr | bond | 4-F—Ph |
| 25c | bond | 1-(t-BuOC=O)pyrrolidin-3-yl | bond | H | bond | Ph |
| 26c | bond | 1,3-C₆H₄ | bond | 3-F—Ph | bond | Ph |
| 27c | bond | 1,3-C₆H₄ | bond | 4-F—Ph | bond | Ph |
| 28c | bond | 1,3-C₆H₄ | bond | 2-F—Ph | bond | Ph |
| 29c | CHMe | Ph | bond | 3-pyrazolyl | bond | Ph |
| 30c | bond | 2,6-pyridyl | bond | 4-F—Ph | bond | Ph |
| 31c | CHMe | 4-(HOC(Me)₂CH₂—Ph | bond | H | bond | Ph |
| 32c | bond | 1,3-C₆H₄ | bond | 2-NC—Ph | bond | Ph |
| 33c | CHMe | 4-MeO₂C—Ph | bond | H | bond | 4-F—Ph |
| 34c | CHMe | 4-HOC(Me)₂—Ph | bond | H | bond | 4-F—Ph |
| 35c | CHMe | 1,4-C₆H₄ | bond | 4-pyridyl | bond | Ph |
| 36c | CHMe | 1,4-C₆H₄ | bond | 3-pyridyl | bond | Ph |
| 37c | CHMe | 1,4-C₆H₄ | bond | 2,4-diF—Ph | bond | i-Pr |
| 38c | bond | 1,3-C₆H₄ | bond | 2-MeO—Ph | bond | Ph |
| 39c | CHMe | 4-Br—Ph | bond | H | bond | Ph |
| 40c | CHMe | 1,4-C₆H₄ | bond | 2-thienyl | bond | Ph |
| 41c | bond | 1,3-C₆H₄ | bond | 2-Cl—Ph | bond | Ph |
| 42c | bond | 1,3-C₆H₄ | bond | 3-Cl—Ph | bond | Ph |
| 43c | bond | 1,3-C₆H₄ | bond | Ph | bond | 3-Cl—Ph |
| 44c | CHMe | 4-F2HCO—Ph | bond | H | bond | 4-F—Ph |
| 45c | bond | 1,3-C₆H₄ | bond | 2,5-diF—Ph | bond | Ph |
| 46c | bond | 1,3-C₆H₄ | bond | 3,5-diF—Ph | bond | Ph |
| 47c | bond | 1,3-C₆H₄ | bond | 2,4-diF—Ph | bond | Ph |
| 48c | bond | 1,3-C₆H₄ | bond | 4-F—Ph | bond | Ph |
| 49c | CHMe | 4-Br—Ph | bond | H | bond | 2-thienyl |
| 50c | bond | 1,3-C6H4 | bond | 2,4-diF—Ph | bond | 2-pyridyl |
| 51c | bond | 2,6-pyridyl | bond | 4-F—Ph | bond | 4-F—Ph |
| 52c | bond | 2,6-pyridyl | bond | 4-F—Ph | bond | 2-F—Ph |
| 53c | bond | 2,6-pyridyl | bond | 2,4-diF—Ph | bond | Ph |
| 54c | CHMe | 3-CF3—Ph | bond | H | bond | 4-F—Ph |
| 55c | CHMe | 4-CF3—Ph | bond | H | bond | 4-F—Ph |
| 56c | CHEt | 4-Br—Ph | bond | H | bond | Ph |
| 57c | CHMe | 1,4-C₆H₄ | bond | 2-oxo-5-(1,2-dihydropyridyl) | bond | Ph |
| 58c | CHMe | 1,4-C₆H₄ | bond | 1-oxo-3-pyridyl | bond | Ph |
| 59c | CHMe | 1,4-C₆H₄ | bond | 4-F—Ph | bond | Ph |
| 60c | CHMe | 1,4-C₆H₄ | bond | 3-pyridyl | bond | 4-F—Ph |
| 61c | CHMe | 1,4-C₆H₄ | bond | 5-F-3-pyridyl | bond | Ph |
| 62c | CHMe | 4-Br—Ph | bond | H | bond | 4-F—Ph |
| 63c | CHMe | 1,4-C₆H₄ | bond | 4-F—Ph | bond | 2-thienyl |
| 64c | bond | 1,3-C₆H₄ | bond | 2-Cl-4-F—Ph | bond | Ph |

| | | | | | | |
|---|---|---|---|---|---|---|
| 65c | bond | 2,6-pyridyl | bond | 2-Cl-4-F—Ph | bond | Ph |
| 66c | bond | 1,3-(4-F)C6H3 | bond | 4-F—Ph | bond | 4-F—Ph |
| 67c | bond | 1,3-(4-F)C6H3 | bond | 4-F—Ph | bond | 2-F—Ph |
| 68c | bond | 2,6-pyridyl | bond | 2,4-diF—Ph | bond | 4-F—Ph |
| 69c | bond | 2,6-pyridyl | bond | 2,4-diF—Ph | bond | 2-F—Ph |
| 70c | CHMe | 1,4-$C_6H_4$ | bond | 4-morpholinyl | bond | 4-F—Ph |
| 71c | CHMe | 1,4-$C_6H_4$ | bond | 2-MeO-5-pyridyl | bond | Ph |
| 72c | CHMe | 1,4-$C_6H_4$ | bond | 1-Me-6-oxo-3-(1,6-dihydropyridyl) | bond | Ph |
| 73c | CHEt | 1,4-$C_6H_4$ | bond | 4-F—Ph | bond | Ph |
| 74c | CHMe | 1,4-$C_6H_4$ | bond | 2-Me-4-pyridyl | bond | 4-F—Ph |
| 75c | CHEt | 4-Br—Ph | bond | H | bond | 4-F—Ph |
| 76c | CHMe | 1,4-$C_6H_4$ | bond | 4-F—Ph | bond | 4-F—Ph |
| 77c | CHMe | 1,4-$C_6H_4$ | bond | 2,4-diF—Ph | bond | Ph |
| 78c | CHMe | 1,4-$C_6H_4$ | bond | 4-F—Ph | bond | 3-F—Ph |
| 79c | CHMe | 1,4-$C_6H_4$ | bond | 4-F—Ph | bond | 2-F—Ph |
| 80c | CHMe | 1,4-$C_6H_4$ | bond | 5-F-3-pyridyl | bond | 4-F—Ph |
| 81c | CHMe | 1,4-$C_6H_4$ | bond | 5-Me-1,3,4-thiadiazol-2-yl | bond | 4-F—Ph |
| 82c | bond | 1,3-$C_6H_4$ | bond | 2,6-diCl—Ph | bond | Ph |
| 83c | CHMe | 1,4-$C_6H_4$ | bond | 2,4-diF—Ph | bond | 2-thienyl |
| 84c | bond | 2,6-pyridyl | bond | 2-Cl-4-F—Ph | bond | 4-F—Ph |
| 85c | bond | 2,6-pyridyl | bond | 2-Cl-4-F—Ph | bond | 2-F—Ph |
| 86c | bond | 2,6-(5-Cl)-pyridyl | bond | 4-F—Ph | bond | 2-F—Ph |
| 87c | bond | 1,3-(4-F)$C_6H_3$ | bond | 2,4-diF—Ph | bond | 4-F—Ph |
| 88c | bond | 1,3-(4-F)$C_6H_3$ | bond | 2,4-diF—Ph | bond | 2-F—Ph |
| 89c | CHMe | 1,4-$C_6H_4$ | bond | 5-MeCO-2-thienyl | bond | Ph |
| 90c | CHMe | 1,4-$C_6H_4$ | bond | 5-MeO-3-pyridyl | bond | 4-F—Ph |
| 91c | CHMe | 1,4-$C_6H_4$ | bond | 5-($H_2$NCHMe)-2-thienyl | bond | Ph |
| 92c | CHEt | 1,4-$C_6H_4$ | bond | 2,4-diF—Ph | bond | Ph |
| 93c | CHEt | 1,4-$C_6H_4$ | bond | 4-F—Ph | bond | 4-F—Ph |
| 94c | CHMe | 1,4-$C_6H_4$ | bond | 5-(HOCHMe)-2-thienyl | bond | Ph |
| 95c | CHMe | 1,4-$C_6H_4$ | bond | 2,4-diMe-5-thiazolyl | bond | 4-F—Ph |
| 96c | CHMe | 1,4-$C_6H_4$ | bond | 5-Cl-3-pyridyl | bond | 4-F—Ph |
| 97c | CHMe | 1,4-$C_6H_4$ | bond | 2,4-diF—Ph | bond | 4-F—Ph |
| 98c | bond | 1,3-(4-F)$C_6H_3$ | bond | 2-Cl-4-F—Ph | bond | 4-F—Ph |
| 99c | bond | 2,6-(5-F)-pyridyl | bond | 2,4-diF—Ph | bond | 2-F—Ph |
| 100c | CHEt | 1,4-$C_6H_4$ | bond | 2,4-diF—Ph | bond | 4-F—Ph |
| 101c | CHMe | 1,4-$C_6H_4$ | bond | 3-($CF_3$)-1-pyrazolyl | bond | 4-F—Ph |
| 102c | CHMe | 1,4-$C_6H_4$ | bond | 6-$CF_3$-3-pyridyl | bond | 4-F—Ph |

$^a$$Cy^1$ = 1,3-$C_6H_4$ means

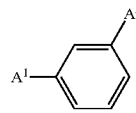

$Cy^1$ = 1,4-$C_6H_4$ means

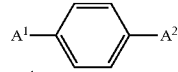

$Cy^1$ = 1,3-(4-F)$C_6H_3$ means

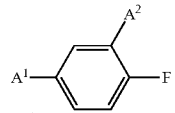

$Cy^1$ = 2,6-(5-Cl)-pyridyl means

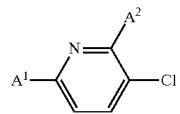

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

The disclosed compounds can be used alone (i.e. as a monotherapy) or in combination with another therapeutic agent effective for treating any of the above indications. The pharmaceutical compositions can comprise the disclosed compounds alone as the only pharmaceutically active agent or can comprise one or more additional pharmaceutically active agents.

A pharmaceutical composition of the invention may, alternatively or in addition to a compound of Formula I, $I_1$-$I_{26}$, $Ia_{1-3}$-$Ij_{1-3}$, comprise a pharmaceutically acceptable salt of a compound of Formula I, $I_1$-$I_{26}$, $Ia_{1-3}$-$Ij_{1-3}$ or a prodrug or pharmaceutically active metabolite of such a compound or salt and one or more pharmaceutically acceptable carriers therefore. Alternatively, a pharmaceutical composition of the invention may comprise a compound of Formula I, $I_1$-$I_{26}$, $Ia_{1-3}$-$Ij_{1-3}$ or a pharmaceutical salt thereof as the only pharmaceutically active agent in the pharmaceutical composition.

A pharmaceutical composition of the invention may, alternatively or in addition to a compound of Formula I, $I_1$-$I_{26}$, $Ia_{1-3}$-$Ij_{1-3}$, comprise a pharmaceutically acceptable salt of a compound of Formula I or a prodrug or pharmaceutically active metabolite of such a compound or salt and one or more pharmaceutically acceptable carriers therefore.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, $I_1$-$I_{26}$, $Ia_{1-3}$-$Ij_{1-3}$ or an enantiomer, diastereomer, or pharmaceutically acceptable salt thereof of composition thereof. As used herein, "treating" or "treatment" includes both therpaeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the liklihood that a subject will then develop the disease or condition in a subject that is at risk for developing the disease or condition.

An embodiment of the invention includes administering an 11β-HSD1 inhibiting compound of Formula I, $I_1$-$I_{26}$, $Ia_{1-3}$-$Ij_{1-3}$ or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I, $I_1$-$I_{26}$, $Ia_{1-3}$-$Ij_{1-3}$ or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify. Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula (I)

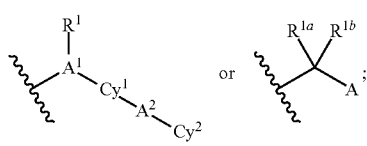

I wherein
R is

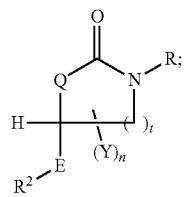

$R^1$ is (a) absent or (b) is selected from $(C_1-C_6)$alkyl, $(C_2-C_6)$alkenyl, $(C_2-C_6)$alkynyl and $(C_1-C_3)$alkoxy$(C_1-C_3)$alkyl, each of which is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, each of which is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl; $(C_1-C_6)$alkylcarbonyl; $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl and oxo;

$Cy^2$ is (a) hydrogen or (b) aryl, heteroaryl, cycloalkyl or heterocyclyl, each of which is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkyl, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl; $(C_1-C_6)$alkylcarbonyl; $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

provided that if (a) $A^1$ is $CH_2CH_2O$; (b) $Cy^1$ is phenyl and (c) $A^2$ is $CH_2$ then $Cy^2$ is not heterocyclyl substituted with oxo;

$R^{1a}$ and $R^{1b}$ are each independently (a) hydrogen or (b) $(C_1-C_6)$alkyl, $(C_2-C_6)$alkenyl, $(C_2-C_6)$alkynyl or $(C_1-C_3)$alkoxy$(C_1-C_3)$alkyl, each of which is optionally substituted with up to three groups independently selected from fluorine, hydroxy, $(C_1-C_3)$alkoxy and $H_2NC(=O)$;

A is straight or branched $(C_1-C_8)$alkyl, $(C_2-C_8)$alkenyl or $(C_2-C_8)$alkynyl, each of which is optionally substituted with up to 4 groups independently selected from fluorine, cyano, oxo, $R^4$, —OH $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4SO_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclylamino (wherein the heterocyclyl portion is optionally substituted by alkyl, haloalkyl or oxo); heteroarylamino (wherein the heteroaryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); arylamino (wherein the aryl portion is optionally substituted by alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and cycloalkylamino (wherein the cycloalkyl portion is optionally substituted by alkyl, haloalkyl or oxo);

t is 3;
Y is $(C_1-C_6)$alkyl or halo$(C_1-C_6)$alkyl;
n is 0, 1 or 2;
E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl and oxo; provided that if Q is NH, then $ER^2$ is not $(C_1-C_6)$alkyl or benzyl;

$R^2$ is $(C_1-C_6)$alkyl, aryl, heteroaryl, cycloalkyl or heterocyclyl, each of which is optionally substituted with up to 4 groups independently selected from fluorine, chlorine, bromine, iodine, nitro, hydroxy, $(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $H_2NCO$, $H_2NSO_2$, $(C_1-C_6)$ alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxyl; (C$_1$-C$_6$)alkylcarbonyl; (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl;

provided that when E is bond and R$^2$ is phenyl, then R$^2$ is not substituted with (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, or halo(C$_4$-C$_7$)cycloalkylalkoxy;

provided that when (a) A$^1$ is bond; (b) R$^1$ is absent; (c) Cy$^1$ is phenyl; (d) A$^2$ is bond (e) Cy$^2$ is H and (f) E is bond, then R$^2$ is not unsubstituted phenyl;

Q is NR$^5$;

each R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl; and each R$^5$ is independently H, (C$_1$-C$_6$)alkyl, halo(C$_1$-C$_6$)alkyl, or hydroxy(C$_1$-C$_6$)alkyl;

or a pharmaceutically acceptable salt, enantiomer or diastereomer thereof.

2. The compound of claim 1, wherein the compound is of Formula (I$_1$)

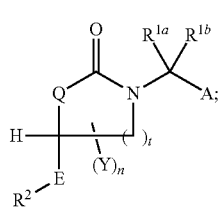

or a pharmaceutically acceptable salt, enantiomer or diastereomer thereof.

3. The compound of claim 1, wherein the compound is of Formula (I$_{14}$)

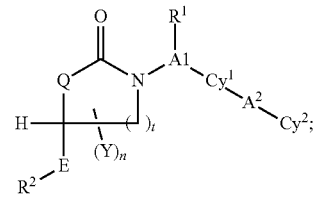

or a pharmaceutically acceptable salt, enantiomer or diastereomer thereof.

4. The compound of claim 1, wherein:

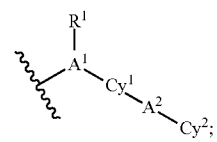

R is

R$^1$ is absent or is methyl or ethyl;

A$^1$ is a bond or CH$_2$;

Cy$^1$ is phenyl, cyclohexyl, pyridyl, N-oxo-pyridyl, thiazolyl or pyrimidinyl, each of which is optionally substituted with 1 to 4 groups independently selected from halo, methyl, trifluoromethyl, hydroxy, methoxy, methoxycarbonyl, carboxy, ethoxycarbonylmethoxy and 2-hydroxy-2-methylpropoxy;

A$^2$ is a bond, O or OCH$_2$CO;

Cy$^1$ is (a) hydrogen or (b) phenyl, thienyl, pyridyl, N-oxopyridyl, cyclopropyl, piperidinyl or piperazinyl, each of which is optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl and tetrazolyl;

n is 0;

E is a bond or CH$_2$;

R$^2$ is phenyl or pyridyl, each of which is optionally substituted with one group selected from halo, methyl, methylthio and (4-morpholino)methyl.

5. The compound of claim 1, wherein R is

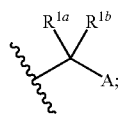

R$^{1a}$ is methyl or ethyl;

R$^{1b}$ is methyl or hydrogen;

A is methyl, ethyl, isopropyl or t-butyl;

n is 0;

E is a bond or CH$_2$; and

R$^2$ is phenyl, thienyl or pyridyl each of which is optionally substituted with halo or methyl.

6. The compound of claim 1, wherein R is

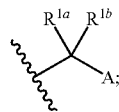

$R^{1a}$ is methyl;
$R^{1b}$ is hydrogen or methyl;
A is methyl or t-butyl;
n is 0;
E is a bond; and
$R^2$ is phenyl or 4-fluorophenyl.

7. 1-((S)-1-(4-bromophenyl)ethyl)-4-phenyl-1,3-diazepan-2-one; or a pharmaceutically acceptable salt, enantiomer or diastereomer thereof.

8. A method of treating a subject with a disease or disorder selected from diabetes mellitus, obesity, glucose intolerance, hyperglycemia, hypertension, insulin resistance, dyslipidemia, atherosclerosis, Cushing's syndrome, visceral fat obesity associated with glucocorticoid therapy, cognitive decline, or metabolic syndrome, comprising the step of administering to the subject an effective amount of the compound of claim 1.

9. The method of claim 8, wherein the disease is type II diabetes mellitus.

10. A pharmaceutical composition comprising: i) a pharmaceutically acceptable carrier or diluent; and ii) the compound of claim 1; or a pharmaceutically acceptable salt, enantiomer or diastereomer thereof.

11. The compound of claim 1, wherein the compound is of Formula ($I_{25}$)

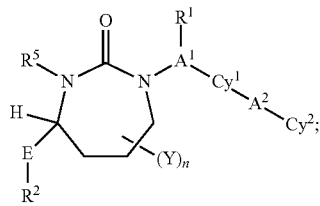

or a pharmaceutically acceptable salt, enantiomer or diastereomer thereof.

12. The compound of claim 1, wherein the compound is of Formula ($Ia_3$)

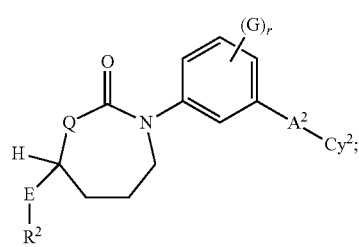

or a pharmaceutically acceptable salt, enantiomer or diastereomer thereof.

13. The compound of claim 1, wherein the compound is of Formula ($Ic_3$)

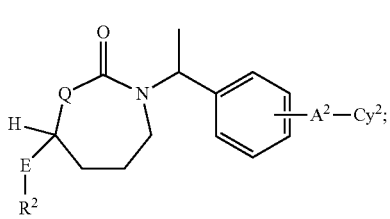

or a pharmaceutically acceptable salt, enantiomer or diastereomer thereof.

14. The compound of claim 1, wherein the compound is of Formula ($Id_3$)

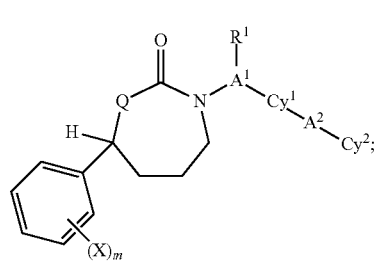

or a pharmaceutically acceptable salt, enantiomer or diastereomer thereof.

15. The compound of claim 1, wherein:
E is a bond or ($C_1$-$C_3$)alkylene, optionally substituted with 1 to 4 groups independently selected from methyl, ethyl, trifluoromethyl or oxo; and when Q is NH, $ER^2$ is not ($C_1$-$C_6$)alkyl substituted with halo, hydroxy or phenyl;
$Cy^1$ is aryl or heteroaryl, optionally substituted with 1 to 4 groups independently selected from fluorine, chlorine, cyano, nitro, hydroxy, carboxy, ($C_1$-$C_6$)alkyl, hydroxy ($C_1$-$C_6$)alkyl, ($C_2$-$C_6$)alkenyl, halo($C_2$-$C_6$)alkenyl, hydroxy($C_2$-$C_6$)alkenyl, ($C_2$-$C_6$)alkynyl, ($C_1$-$C_6$) alkoxy, halo($C_1$-$C_6$)alkoxy, ($C_1$-$C_6$)alkylthio, halo($C_1$-$C_6$)alkylthio, ($C_1$-$C_6$)alkanesulfinyl, halo($C_1$-$C_6$)alkane-sulfinyl, ($C_1$-$C_6$)alkanesulfonyl, halo($C_1$-$C_6$) alkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, ($C_1$-$C_6$)alkylaminosulfonyl, di($C_1$-$C_6$) alkylaminosulfonyl, ($C_1$-$C_6$)alkylcarbonylamino, ($C_1$-$C_6$)alkyl-carbonylamino($C_1$-$C_6$)alkyl, ($C_1$-$C_6$) alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$) alkyl, hydroxy($C_1$-$C_6$)alkoxy, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxyl and ($C_1$-$C_6$)alkylcarbonyl;
$Cy^2$ is meta or para to the ring atom of $Cy^1$ that is bonded to $A_1$; and
$R^2$ is ($C_1$-$C_6$)alkyl, aryl, heteroaryl, cycloalkyl or heterocyclyl, each is optionally substituted with up to 4 groups, independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkane-sulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl, wherein the aryl and heteroaryl represented by $R^2$ are substituted only meta or para to the ring atom attached to E.

* * * * *